(12) United States Patent
Thakor et al.

(10) Patent No.: US 7,299,088 B1
(45) Date of Patent: Nov. 20, 2007

(54) APPARATUS AND METHODS FOR BRAIN RHYTHM ANALYSIS

(76) Inventors: Nitish V Thakor, 12010 Misty Rise Ct., Clarksville, MD (US) 21029; Anastasios Bezerianos, Navarinou 26, 262 22, Patras (GR); Feras Al Hatib, 247 Saint Vincent, Irvine, CA (US) 92618; Hasan Al-Nashash, School of Engineering, American University of Sharjah, P.O. Box 26666, Sharjah, U.A.E. (AE); Joseph Paul, 103 Clemento Rd., BLKA-03-07, Singapore (SG); David Sherman, 2307 Covered Bridge Garth, Parkville, MD (US) 21234; Shanbao Tong, 329 W. 30th St., Baltimore, MD (US) 21211; Santosh Venkatesha, 2369 Flax Ter., Baltimore, MD (US) 21209

( * ) Notice: Subject to any disclaimer, the term of this patent is extended or adjusted under 35 U.S.C. 154(b) by 519 days.

(21) Appl. No.: 10/452,190

(22) Filed: Jun. 1, 2003

Related U.S. Application Data

(60) Provisional application No. 60/385,074, filed on Jun. 2, 2002.

(51) Int. Cl.
*A61B 5/04* (2006.01)
(52) U.S. Cl. ....................................... 600/544
(58) Field of Classification Search ................ 600/382, 600/383, 384
See application file for complete search history.

(56) References Cited

U.S. PATENT DOCUMENTS 6,594,524 B2 * 7/2003 Esteller et al. ................ 607/45

2001/0044573 A1 * 11/2001 Manoli et al. ............... 600/383
2003/0176806 A1 * 9/2003 Pineda et al. ................ 600/544

OTHER PUBLICATIONS

Bruhn et al., "Shannon Entropy Applied to the Measurement of the Electroencaphalographic Effects of Desflurane," Anesthesiology, 2001; 95:30-35.*

Olofsen et al, "The Influence of Remifentanil on the Dynamic Relationship between Sevoflurane and Surrogate Anesthetic Effect Measures Derived from the EEG," Anesthesiology, 2002; 96: 555-564.*

Tang et al., "Detection of spikes in epileptic EEG based on Multiresolution Tsallis' entropy," Sheng Wu Yi Xue Gong Cheng Xue Za Zhi, 2001(3): 378-380 (Abstract).*

Al-Nashash et al., "Wavelet Entropy for Subband Segmentation of EEG During Injury and Recovery" Journal of Biomedical Engineering, 2003(31): 653-658 (received Aug. 15, 2001).*

(Continued)

*Primary Examiner*—Robert L. Nasser
(74) *Attorney, Agent, or Firm*—Konrad Raynes & Victor, LLP; Alan S. Raynes

(57) ABSTRACT

Embodiments include methods and apparatus for determining whether a neurological event has occurred in a subject. An apparatus includes at least one sensor adapted to sense electroencephalogram signals from the subject. The apparatus also includes an electroencephalogram acquisition module adapted to receive the electroencephalogram signals from at least one sensor, and a processing and analysis module adapted to receive signals from the electroencephalogram acquisition module and determine changes in neurological function using entropy analysis.

6 Claims, 16 Drawing Sheets

OTHER PUBLICATIONS

Rosso et al, "Wavelet Entropy: a new tool for analysis of short duration brain electrical signals.," Journal of Neuroscience Methods, 105, 2001, pp. 65-75.*

Yordanova, "Wavelet entropy analysis of event related potentials indicates modality-independent theta dominance," Journal of neuroscience Methods, 117, 2002, pp. 99-109.*

Shannon, C.E., "A Mathematical Theory of Communication," reprinted with corrections from *Bell Syst. Tech. J.*, 27:379-423, 623-656 (Jul., Oct. 1948).

Tsallis, C. et al., "The role of constraints within generalized nonextensive statistics", *Physica A*, 261:534-554 (1998).

Tsallis, C., "Possible Generalization of Boltzmann-Gibbs Statistics", *J. Statistical Physics*, 52:479-487 (1988).

Abe, S., "Correlation induced by Tsallis' nonextensivity", *Physica A*, 269:403-409 (1999).

Santos, R.J.V. dos, "Generalization of Shannon's theorem for Tsallis entropy", *J. Math. Phys.*, 38:4104-4107 (Aug. 1997).

Hotta, M. and Joichi, I., "Composability and Generalized Entropy", published in *Phys. Lett. A*, 262:302-309, (1999).

Abe, S., "Axioms and uniqueness theorem for Tsallis entropy", published in *Phys. Lett. A*, 271:74-79, (2000).

Abe, S. and Rajagopal, A.K., "Nonadditive Conditional Entropy and its Significance for Local Realism", published in *Physica A*, 289:157-164, (2001).

Khinchin, A.I., *Mathematical Foundations of Information Theory*, New York: Dover Publ. (1957).

Cover, T.M. and Thomas, J.A., *Elements of Information Theory*, New York: Wiley, chapters 2 & 9. 2, pp. 12-43 & 224-237 (1991).

*Time Frequency and Wavelets in Biomedical Signal Processing*, Ed. Metin Akay, New York: IEEE Press (1998).

Hayes, M., *Statistical Digital Signal Processing and Modeling*, New York: John Wiley & Sons (1996).

Papoulis, A., *Probability, Random Variables, and Stochastic Processes*, 2nd Edition, New York: McGraw-Hill (1984).

* cited by examiner

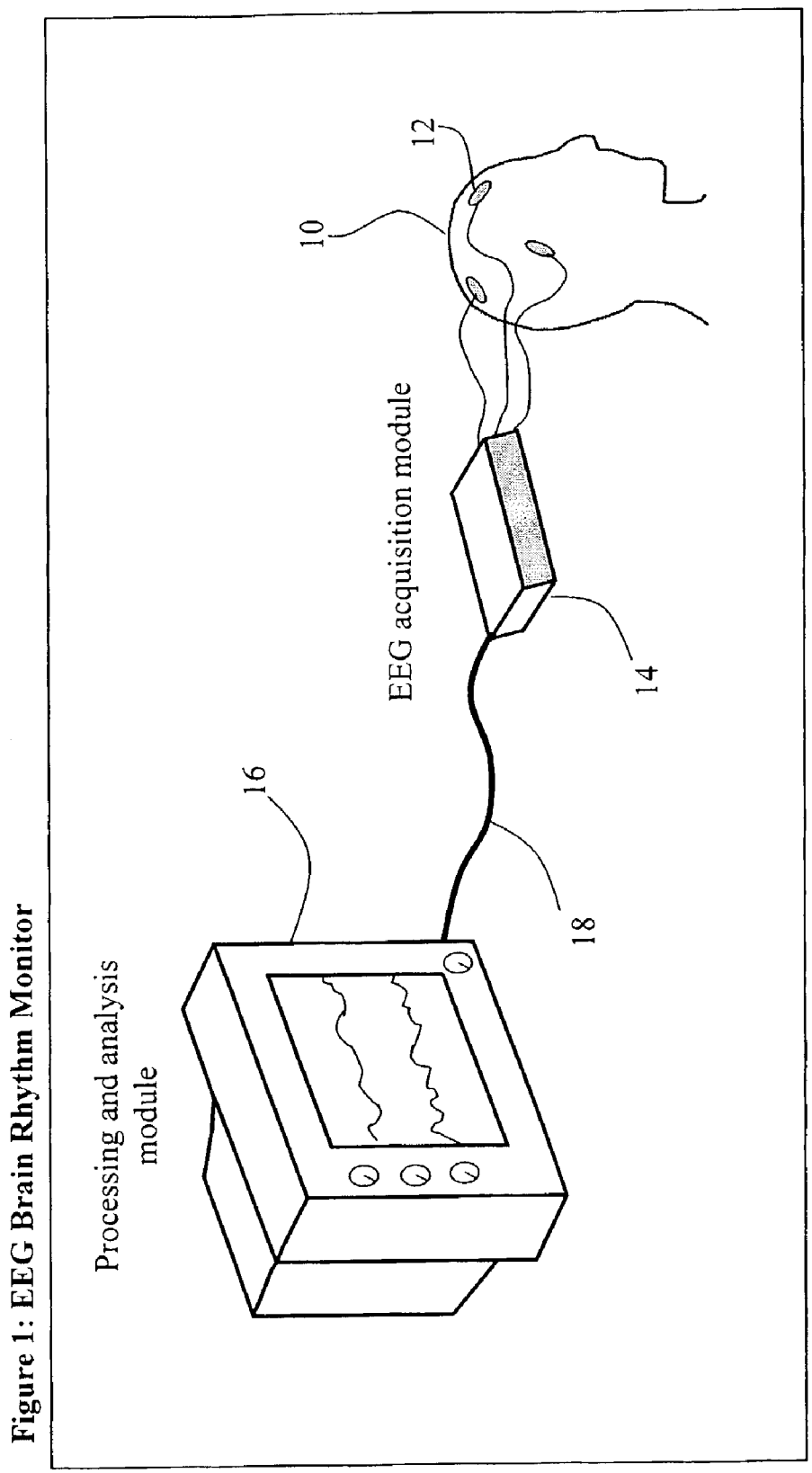
Figure 1: EEG Brain Rhythm Monitor

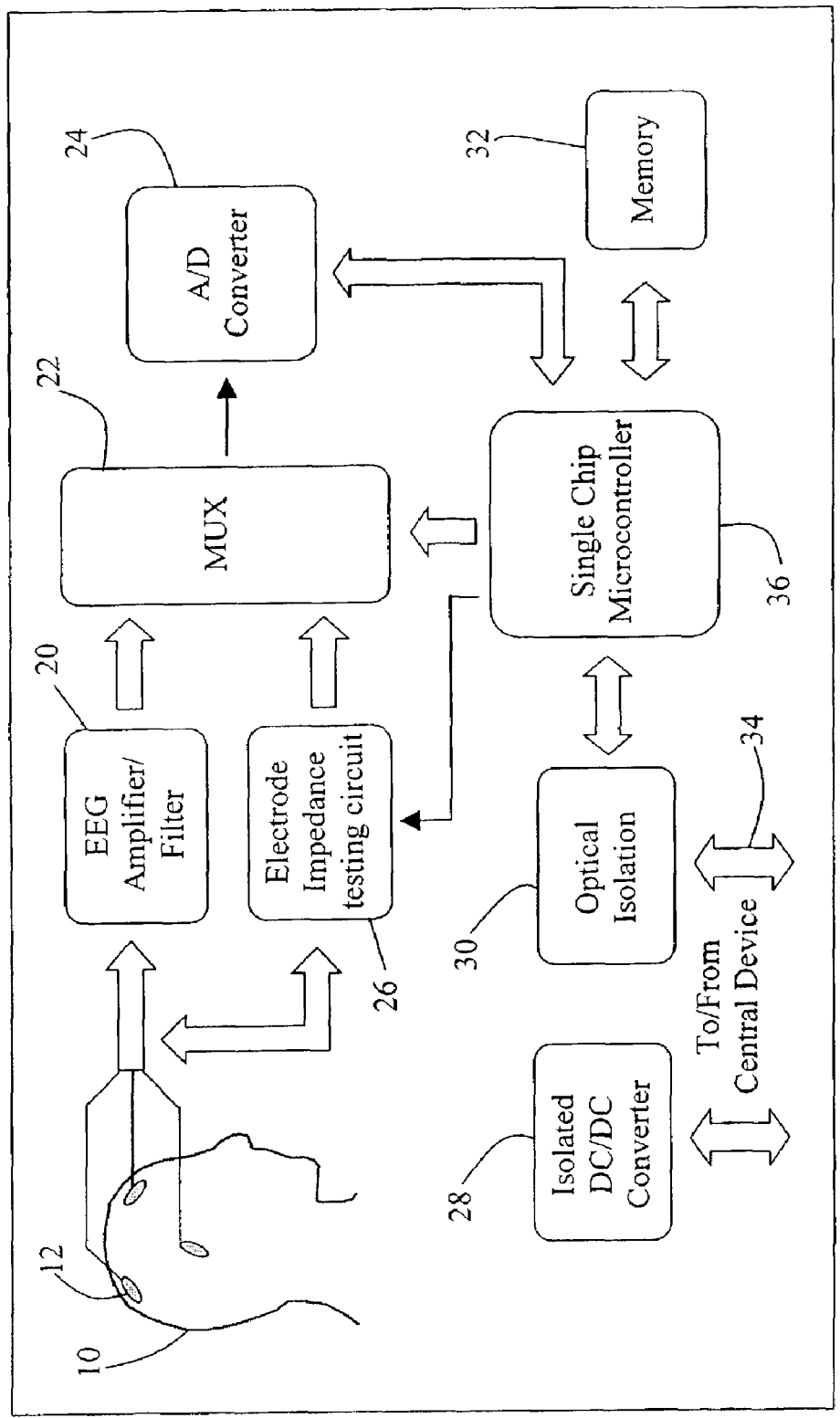
Figure 2: EEG Acquisition Module

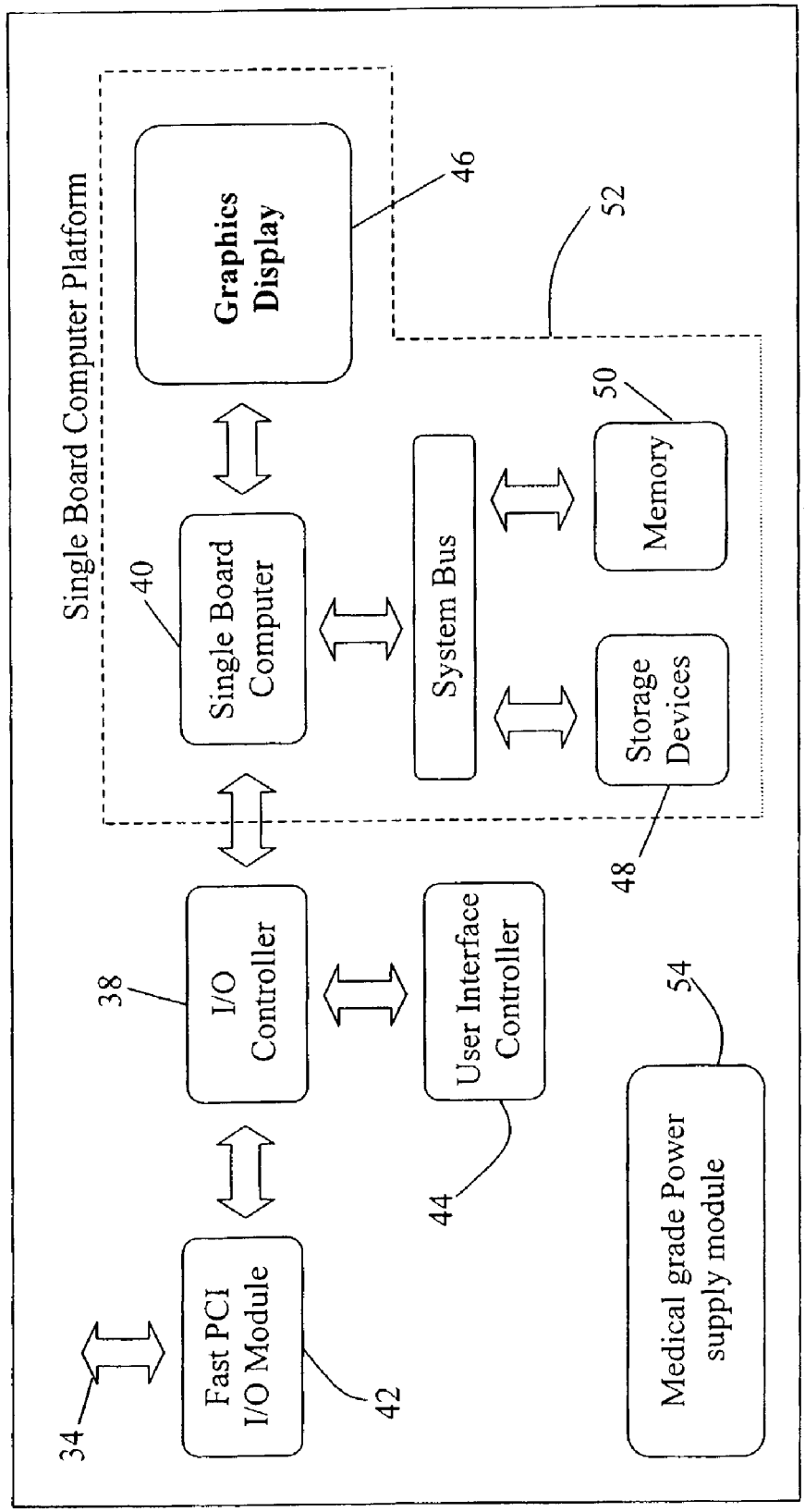
Figure 3: EEG Processing & Analysis Module

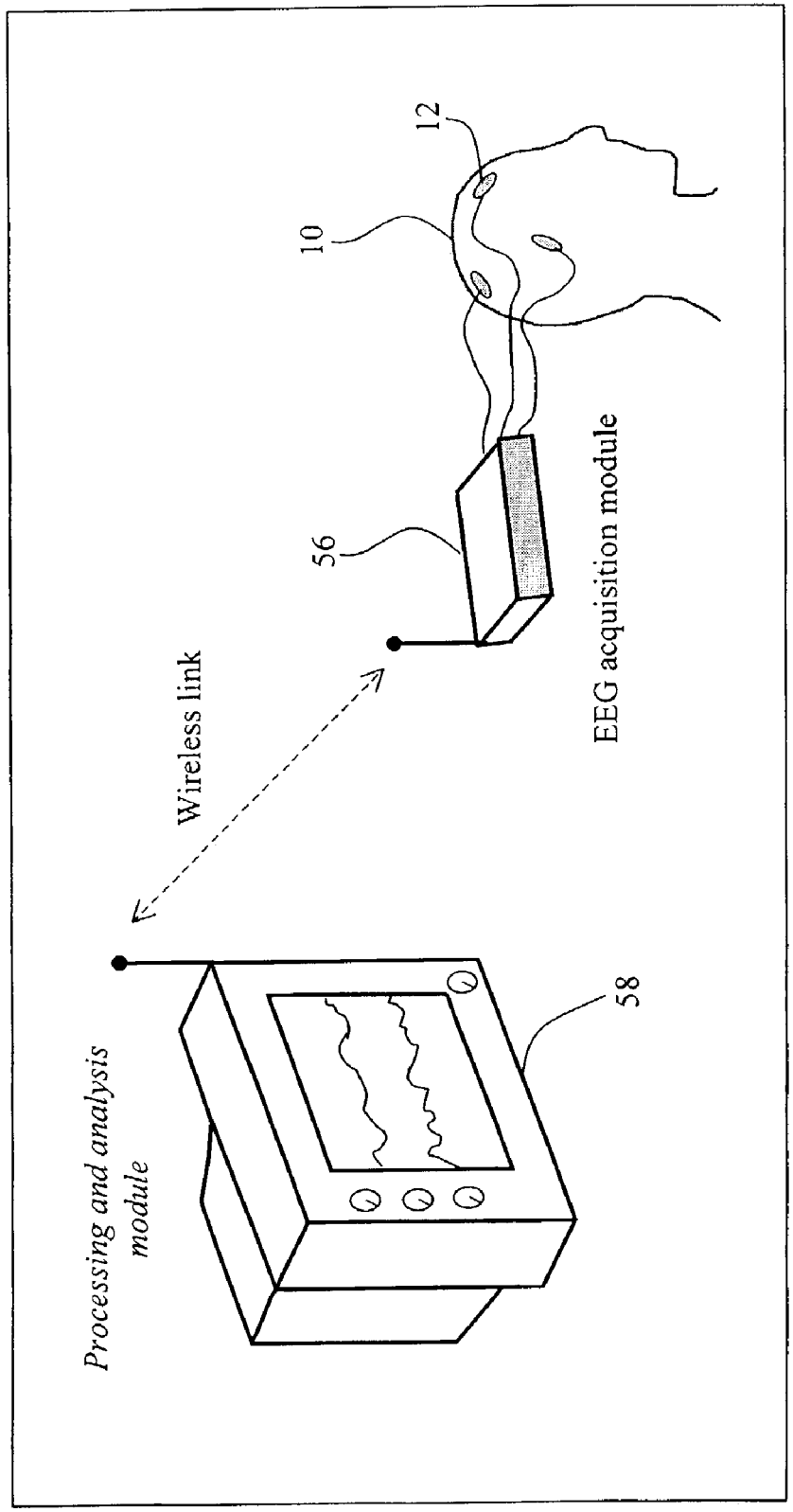
Figure 4: Wireless EEG Brain Rhythm Monitor

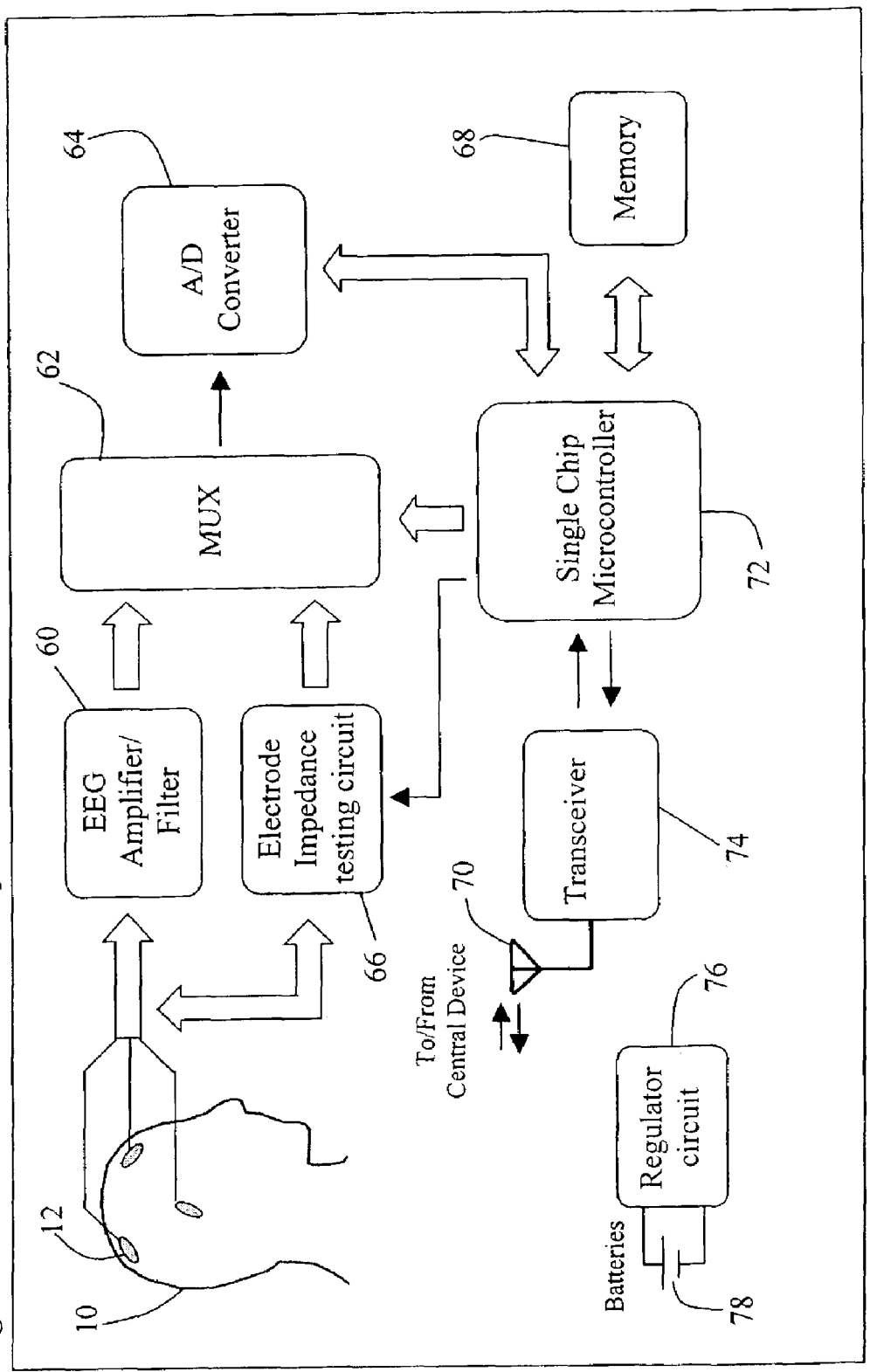
Figure 5: Wireless remote EEG Acquisition Module

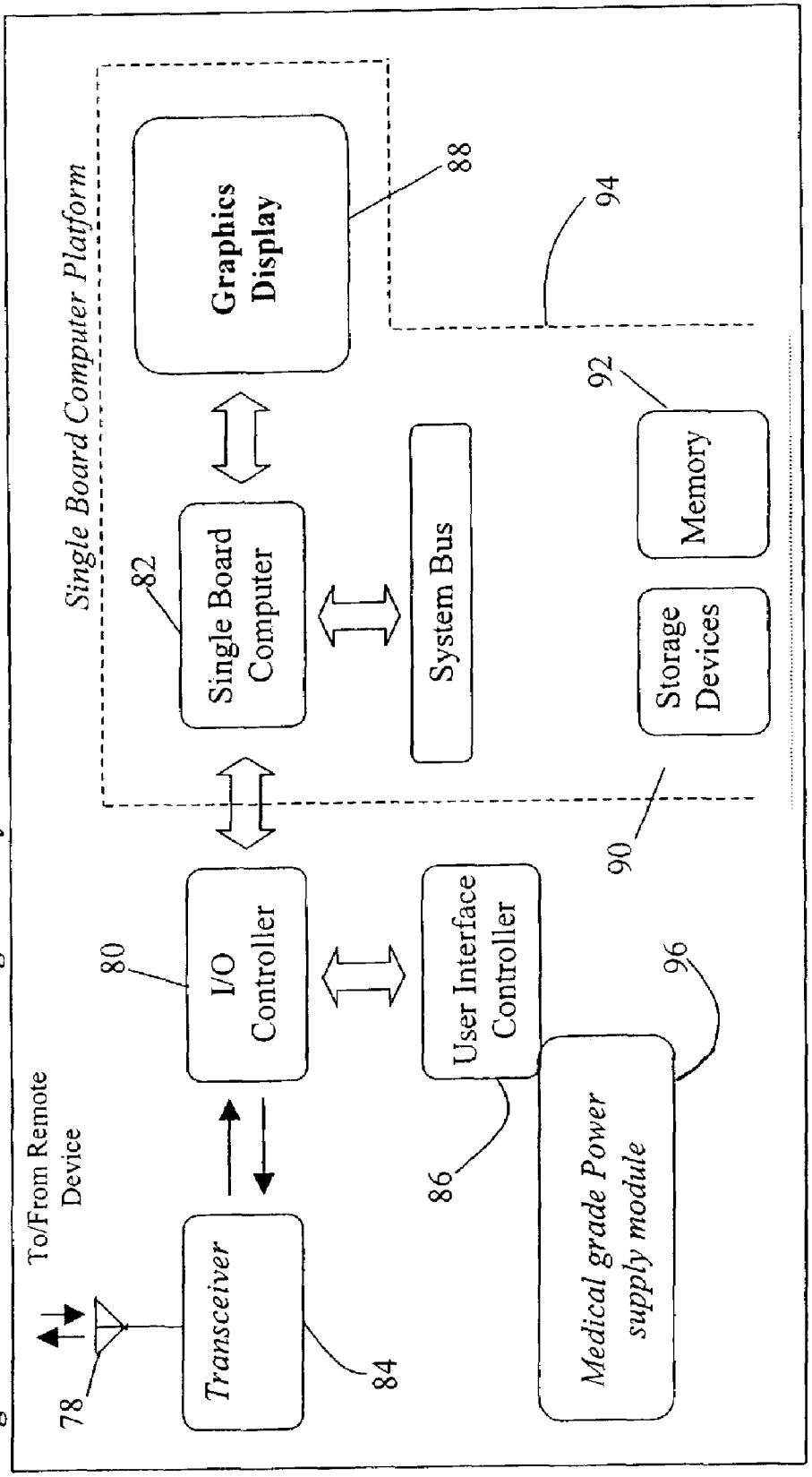
Figure 6: Wireless EEG Processing & Analysis Module

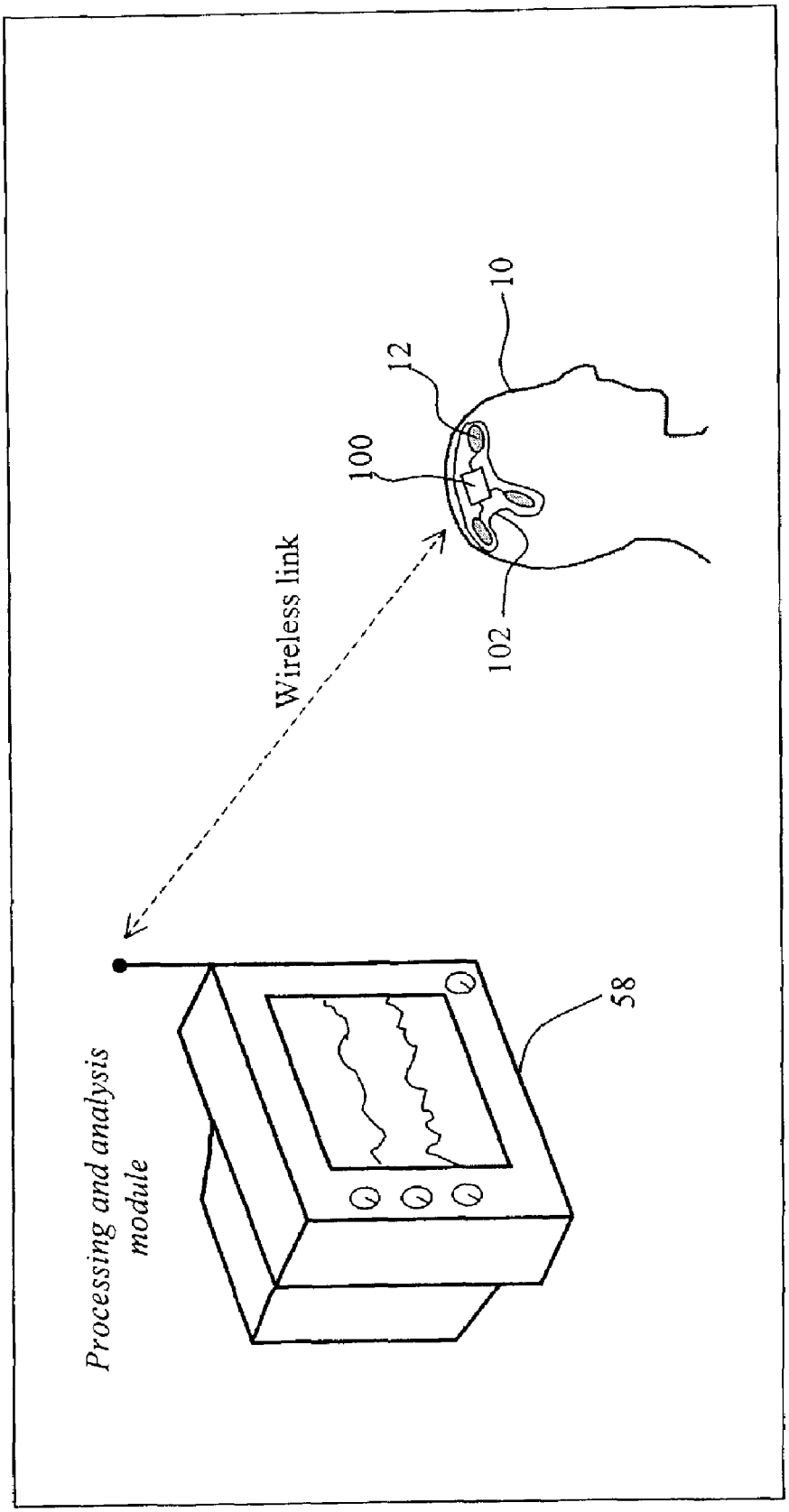

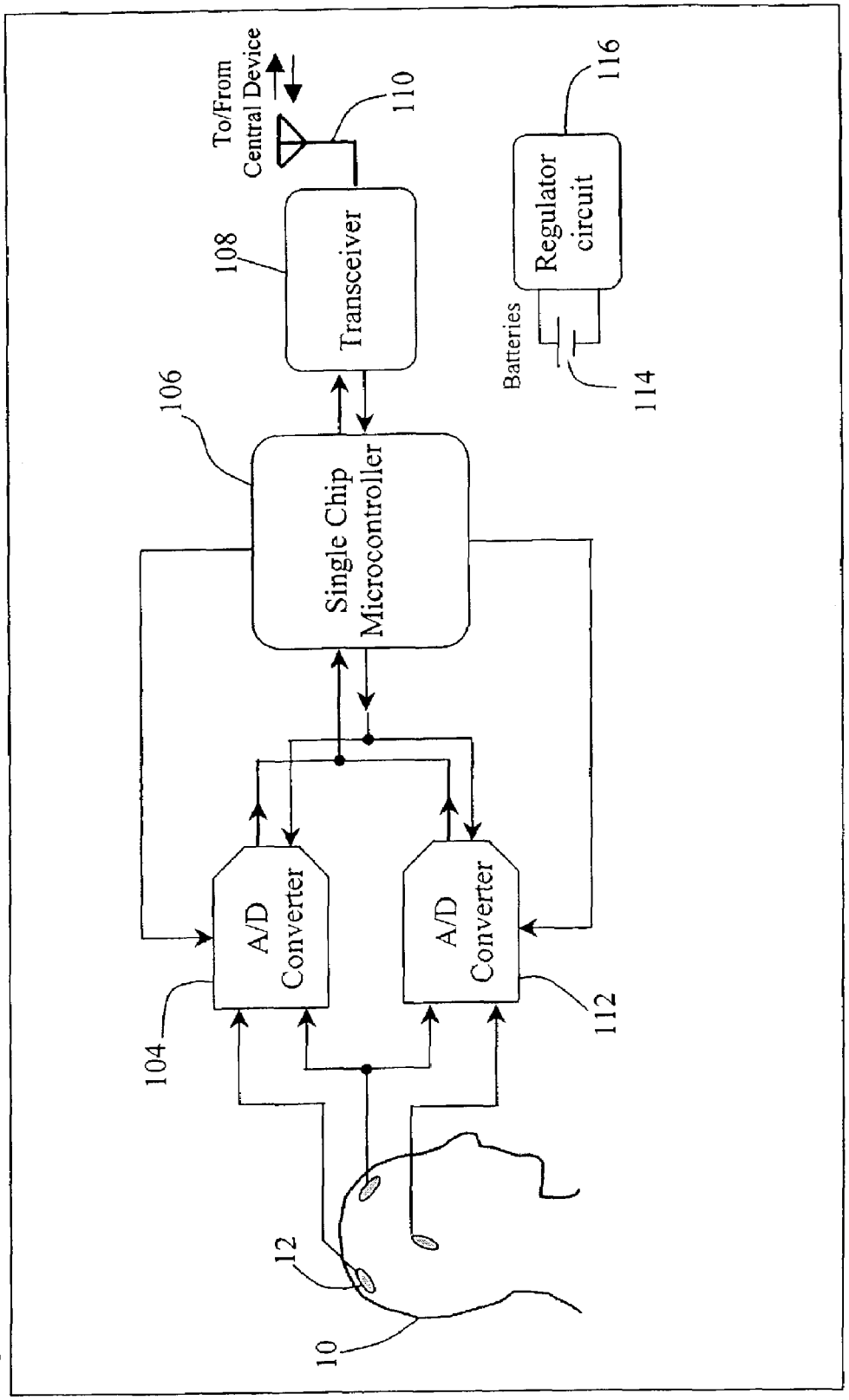
Figure 8: Wireless remote EEG Headcap

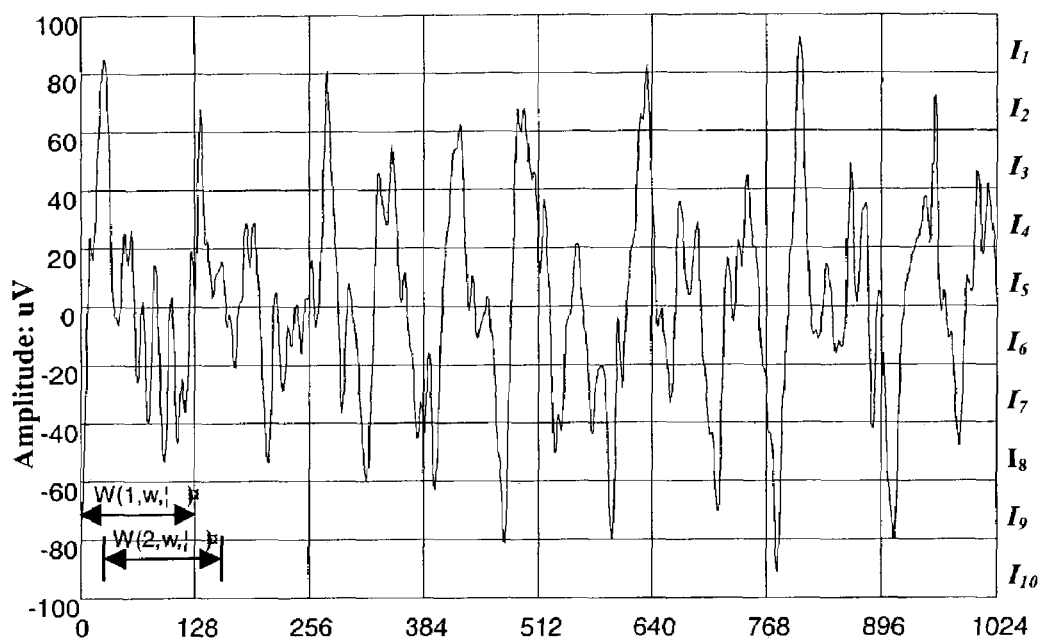
Figure 9: Time Dependent Entropy Estimation
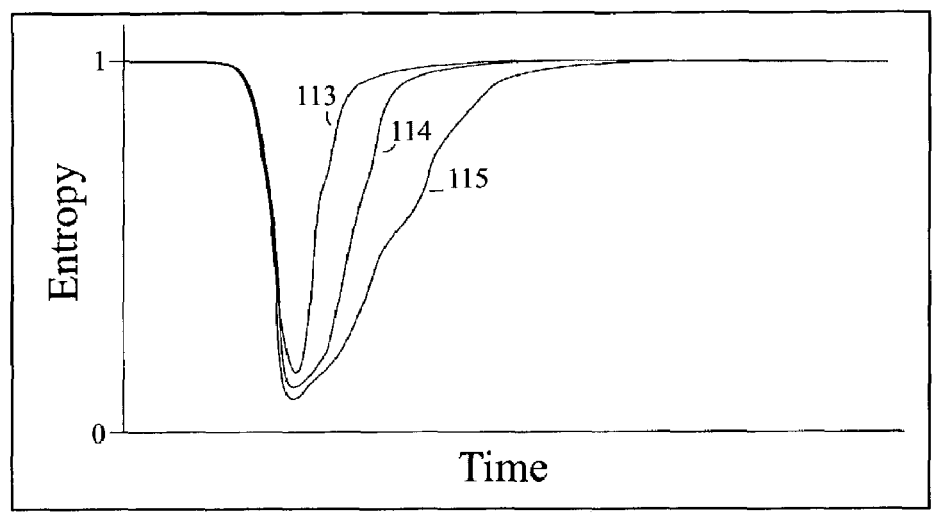
Figure 10: Time Dependent Entropy measures of the brain function.

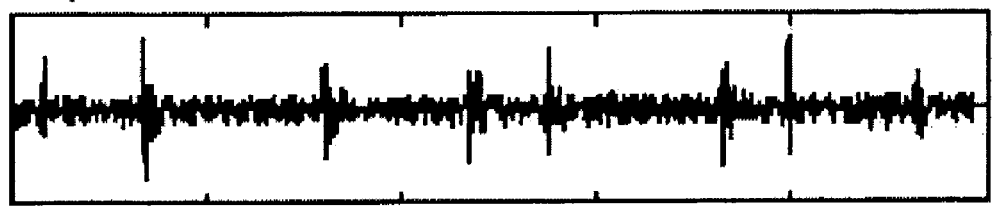
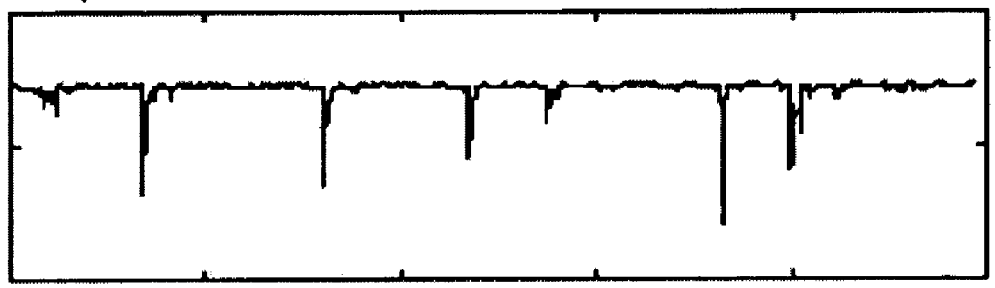
Figure 11: Entropy measure of EEG electical events

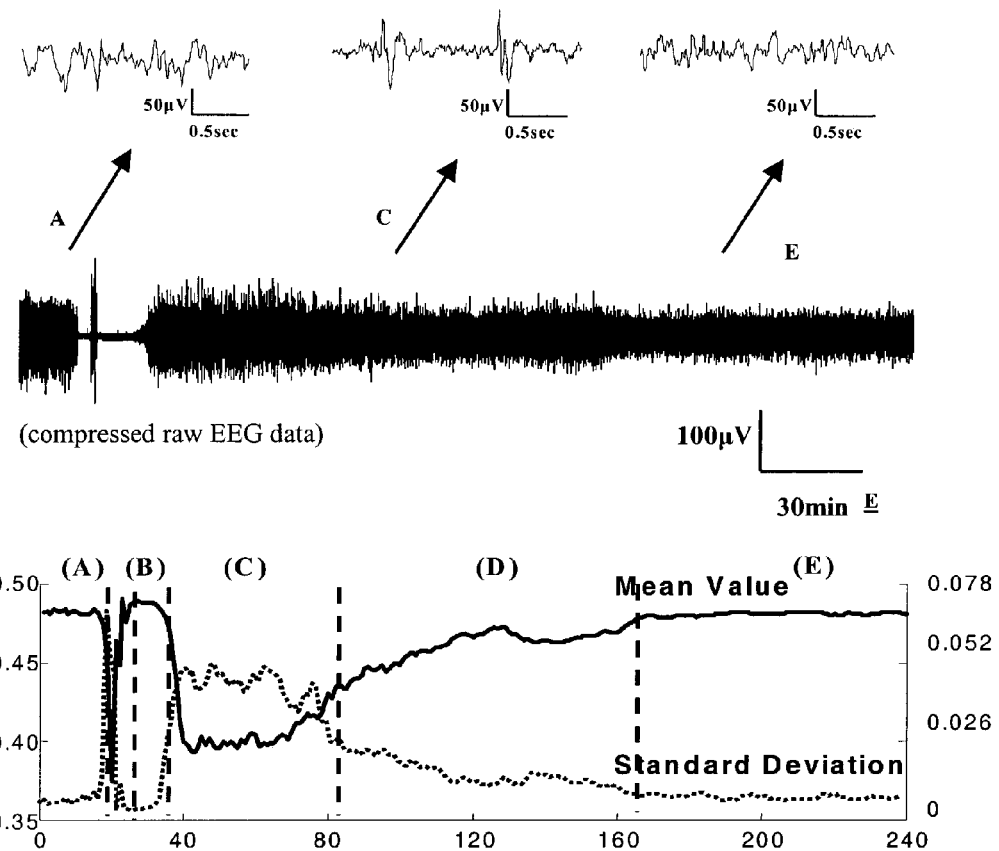
Figure 12: Statistical characteristics of the Entropy Measure
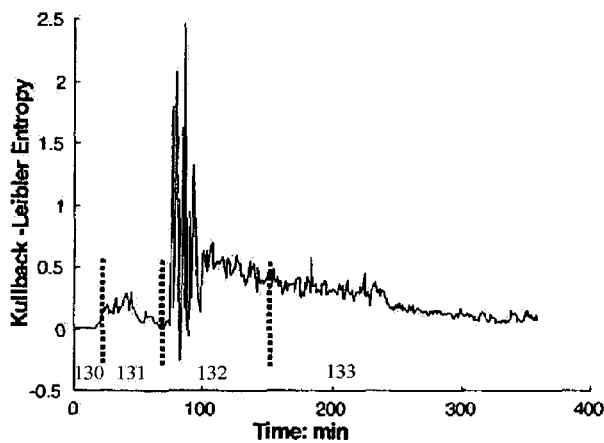
Figure 13: Distance measure of entropy

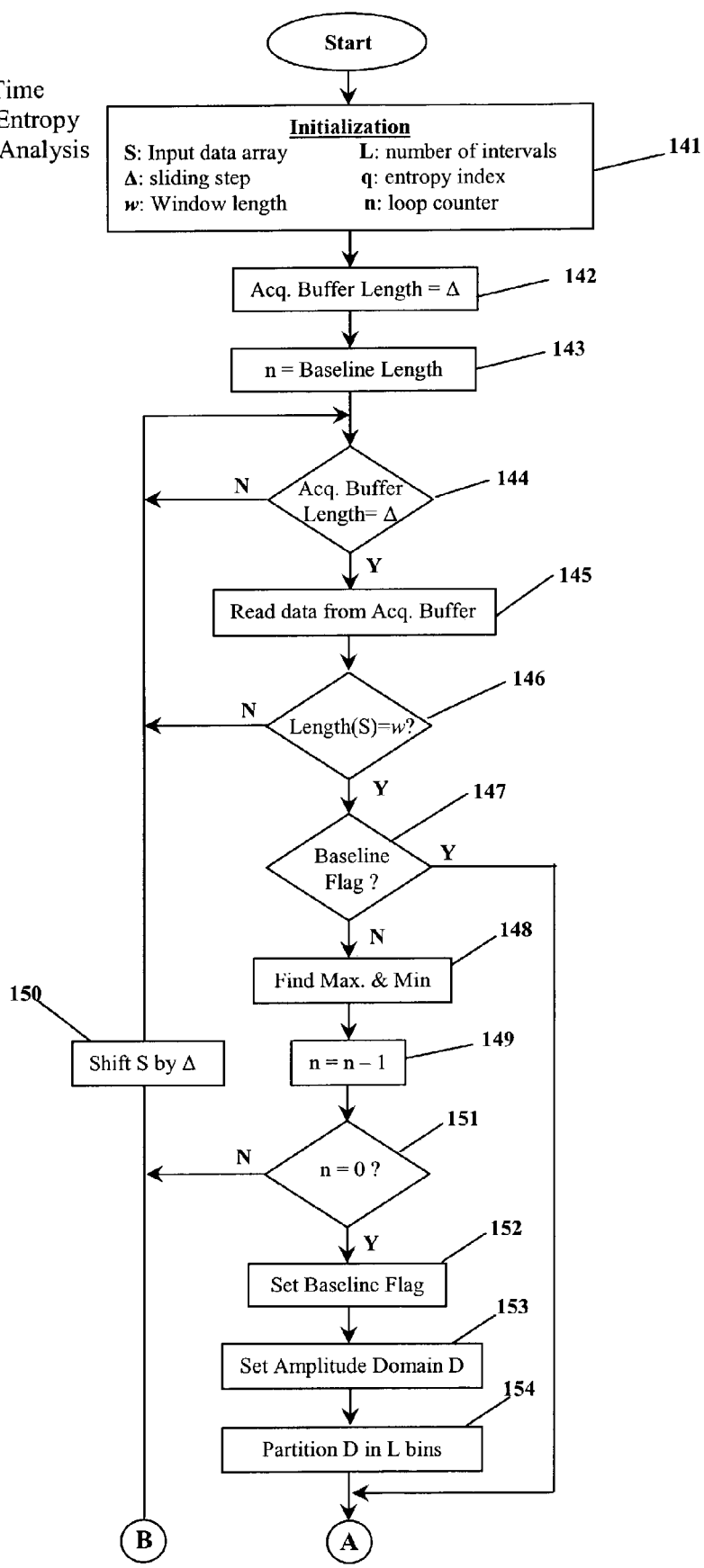
Figure 14: Time Dependent Entropy in the EEG Analysis Module:

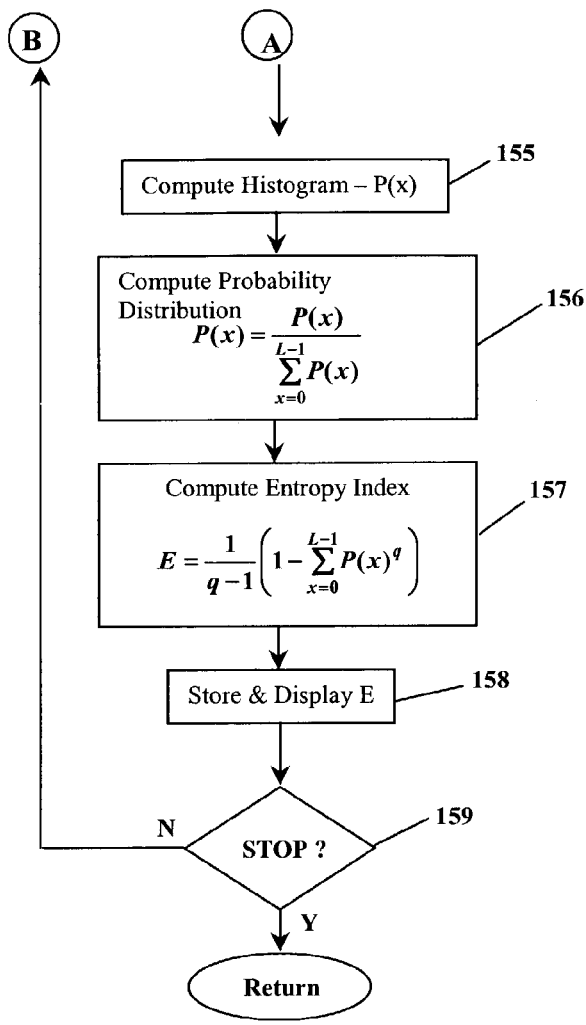
Fig. 14 (cont'd)
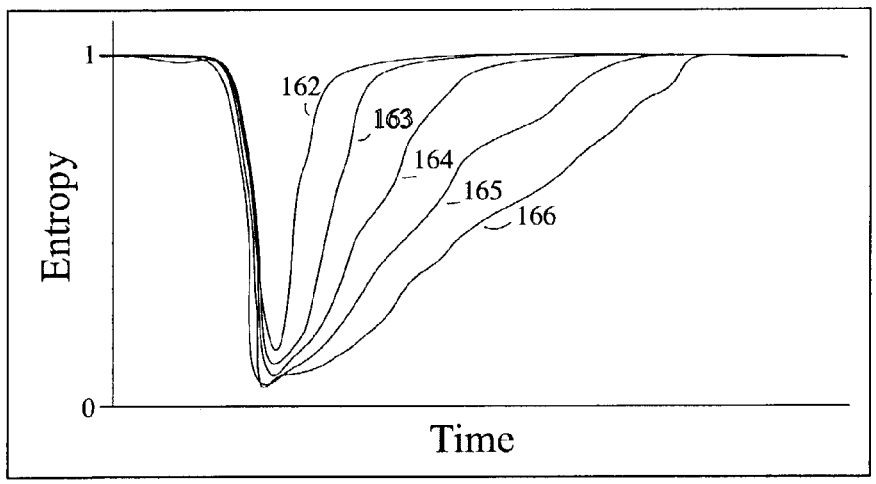
Figure 15: Subband Wavelet Entropy measures of the brain rhythm due to neurological events.

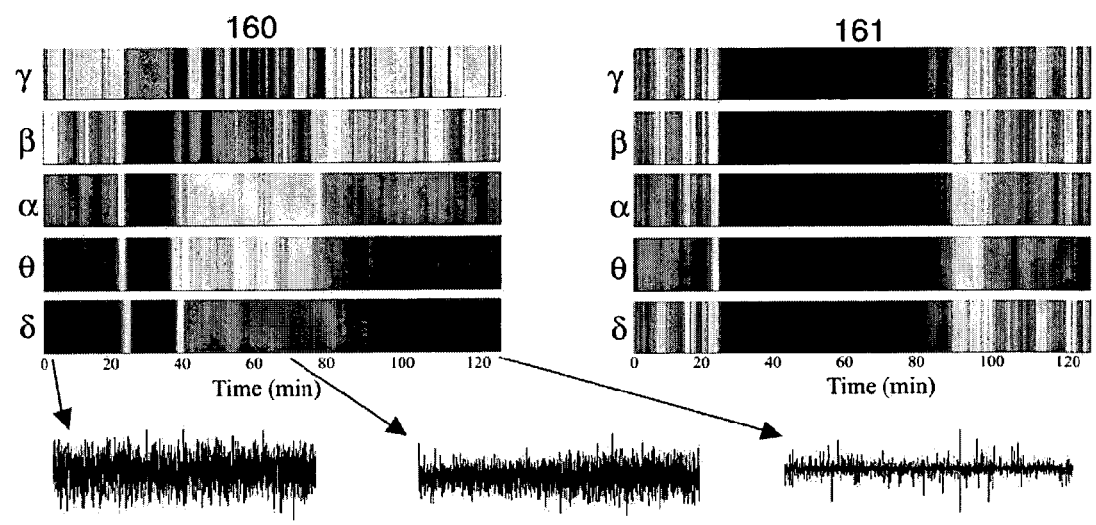
Figure 16: Subband entropy vs Subband energy

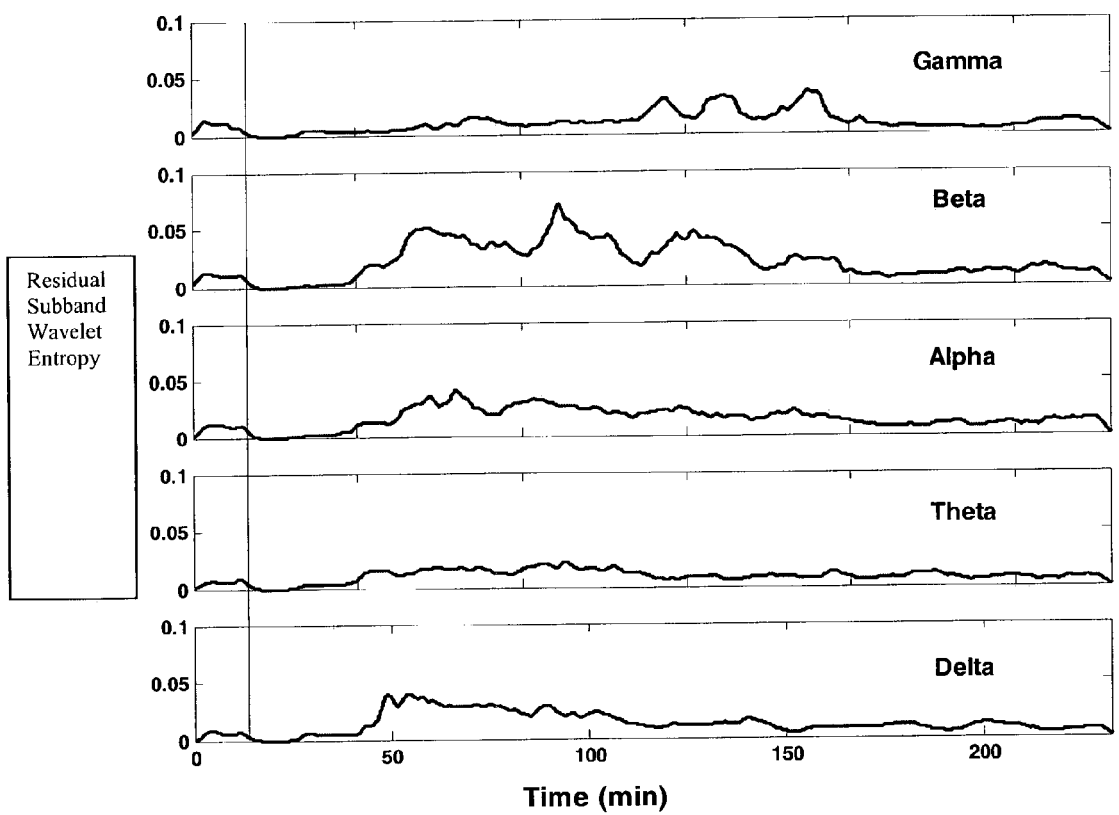
Figure 17. Residual subband wavelet entropy.

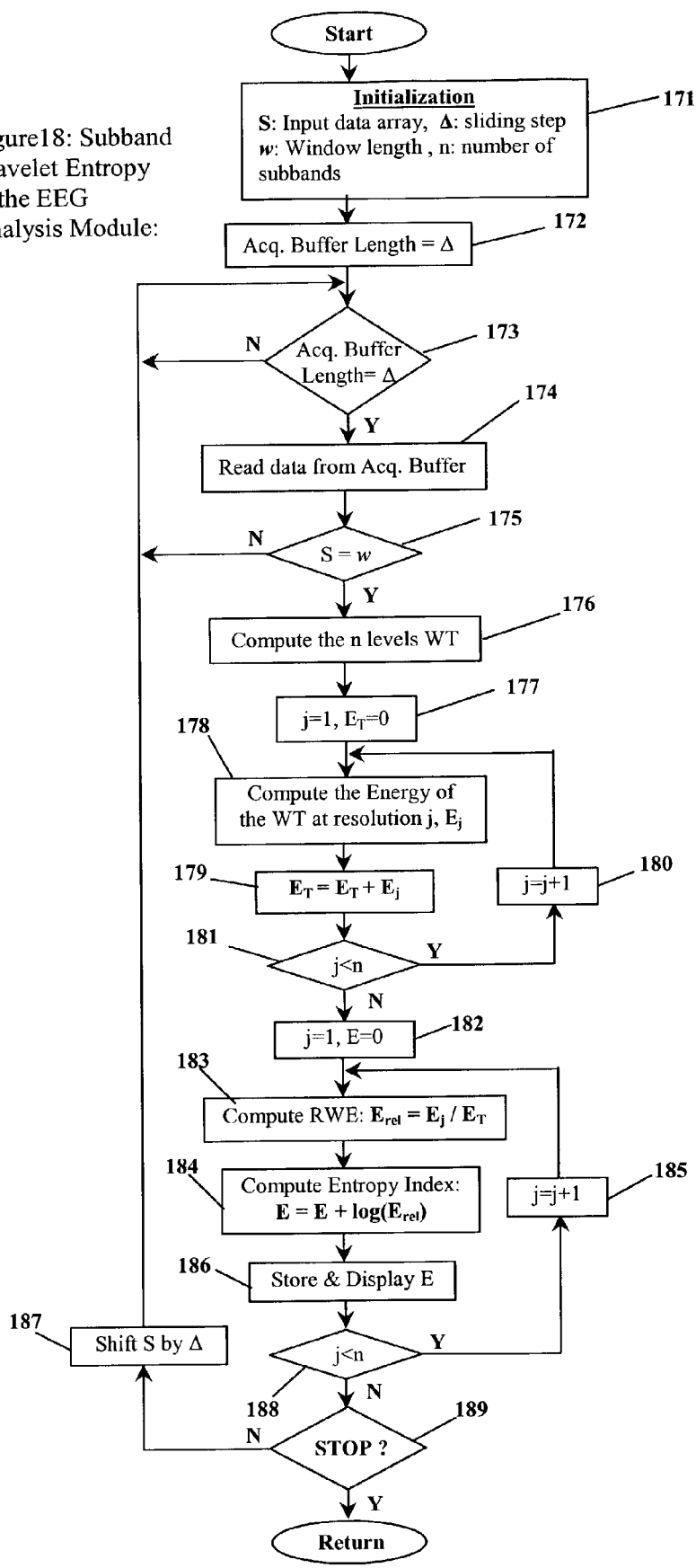
Figure18: Subband Wavelet Entropy in the EEG Analysis Module:

APPARATUS AND METHODS FOR BRAIN RHYTHM ANALYSIS

This application claims the benefit of U.S. Provisional Application No. 60/385,074, filed Jun. 2, 2002, entitled "Apparatus and Methods for Brain Rhythm Analysis". Applicants hereby incorporate by reference U.S. Provisional Application No. 60/385,074, filed Jun. 2, 2002.

The invention was made under contracts with an agency of the U.S. Government under NIH#NS24282 and NIH#HL70129.

FIELD OF INVENTION

Certain embodiments of the present invention relate to brain monitoring.

RELATED INFORMATION

The value of EEG-based monitoring to quantify cortical response is compelling. EEG has been used extensively in performing clinical studies and has been shown to be a sensitive but non-specific measure of brain function. EEG is widely used in a variety of clinical applications. These include a response to normal cognitive function, attentional, fatigue, etc. EEG is also responsive to the state of wakefulness (sleep). Different sleep stages result in changes in the EEG rhythm that can be utilized for sleep response studies. EEG is very responsive to anesthetic levels. Various anesthetics and depth of anesthesia alter the EEG signal features. Visual or quantitative analysis of EEG is useful in determining the anesthetic level, depth or state of consciousness. Indeed EEG responds to the level of consciousness or coma or eventually brain death. In clinical studies, EEG is very useful in diagnosing various neurological disorders and diseases. One of the most studied areas is epilepsy and seizure. Epilepsy results in spikes, bursts and other features can be seen in the EEG signal. Short term changes in EEG are indicative of epileptic even that is ongoing. Long term events may also be indicative of onset or impending epileptic events. EEG is also used in detecting or diagnosing other neurological disorders or indications of brain injury. Indeed, a very appropriate and powerful use of EEG and cortical rhythm analysis in general is to study response to brain injury. Brain injury may take place in a variety of manners, such as focal or global ischemia, stroke, coma, surgical injury, epileptic focus as a byproduct of brain injury, and so on. Detection of brain injury is critical in various clinical environments such as neurological intensive care unit and operating room. Indeed, the application of continuous EEG monitoring may be found in ambulatory and other pre-clinical or clinical monitoring. Critical to recording and analysis of all such EEG rhythms is its computer based acquisition and digitization and subsequent mathematical and quantitative analysis approaches.

The electroencephalogram (EEG) is known to be of value in predicting outcome after ischemic brain injury, most likely because oxygen deprivation affects synaptic transmission, axonal conduction, and cellular action potential firing in a sequential manner. Two findings account for this sensitivity. First, the extent and duration of ischemic injury is reflected in the degree of initial slowing of the background rhythm. Second, severe injury is associated with substantial impairment of cortex and thalamus cellular networks: this chronic impairment is directly reflected in a slow low voltage EEG, and in its most severe form in absence of the somatosensory evoked potential. Injury from cerebral ischemia can also appear in the cortical signal as any of the following EEG waveforms: cerebro-electrical silence, non-reactive alpha, triphasic waves, periodic spiking and other burst-suppression patterns. Thus, routine clinical EEG has some diagnostic value and a strong rationale exists for using the sensitivity of the EEG to assess the degree of cerebral ischemia.

Various mathematical methods and computer algorithms analyze electroencephalogram (EEG) rhythms. The most conventional approach is that of spectral analysis. Digitized EEG signal is analyzed using methods such as Fast Fourier Transform or using filters to separate EEG into different frequency bands, commonly known as delta, theta, alpha, beta, gamma ($\delta$, $\theta$, $\alpha$, $\beta$, $\gamma$). EEG interpretation or display is done by presentation of amplitude or power in these frequency bands. More advanced signal processing methods provide improve approaches for calculating the spectrum and other features. Of importance in clinical applications is whether there is a change in the EEG signal. Graded changes may be used, for example, to diagnose the time or degree of brain injury causing such a change. Characterizing the brain's response as measured by EEG through "linear" indicators provides quantitative indication of graded changes in brain function. Autoregressive modeling can be used to form a compact spectral representation of stationary portions of the EEG. Thus, through autoregressive modeling, meaningful information about certain signals may be encoded in a very compact and accurate way—allowing easy access to their important features. Deviations from normal spectral shape characteristic will be registered through the use of distance measures. Though autoregressive analysis, the cepstrum (log of the spectrum) and critical spectral parameters can also be derived without regard to band power. Such mathematical rhythm analysis is not only a very useful approach to determining changes in EEG rhythms during any brain injury but also during recovery. The mathematical measure such as spectral or cepstral distance would indicate whether there is an ongoing injury related change.

However, the distance measures (spectral distance or cepstral distance) are not specific enough to track the recovery profile of EEG. Comparison with baseline power is needed, which is usually not available. Moreover, the distance metrics are not sensitive to the rapidly changing signal statistic (non-stationarities) of the recovering EEG and they do not give any clue about the different segments of the EEG as it appears after the injury.

In order to overcome limitations of the methods described above, measures of signal statistics that are independent of signal amplitude or power are needed. Also, measures that are not dependent on baseline, which may not always be available, are needed. An approach presented here is to use entropy as a measure of signal statistics, embodying in mathematical terms the randomness or moment to moment statistical fluctuation of signal or any derived parameters from the signal. Unlike the computation of signal power by methods of Fourier transform, the entropy measures are independent of the power changes. This is because the entropy is invariant under the addition of a constant to the signal and under the multiplication of this same signal by a constant different from zero. Also the entropy estimated for the current window is tightly linked to the measurements obtained from a fixed number of the past time windows. It is therefore appropriate to derive a quantitative measure based on the entropy, a rigorous measure of the information content within the signal channels, than to use indicators based on signal power or distance metrics.

SUMMARY OF THE INVENTION

Certain embodiments of the invention relate to an apparatus including one or more electrodes, electronic instrumentation and a computer to record and analyze brain rhythms. Certain embodiments also relate to mathematical methods for analyzing the brain rhythms. Certain method embodiments described herein depend on the analysis of the brain rhythm called electroencephalogram (EEG) which has been digitized and acquired by a computer. Methods of recording may involve a variety of electrodes placed either directly on the head or the scalp, or on to of the brain tissue itself, or in the depths of the brain using a variety of electrodes and instrumentation. Certain embodiments describe a variety of related methods to analyze digitized EEG rhythms. The methods of analysis may look at the amplitude, frequency and/or other statistical fluctuations and may use methods that determine the entropy or the information content of the brain rhythm waveform. The methods of analysis of the digitized brain rhythms may include time, frequency, wavelet and/or other forms of entropy to provide a mathematical description of the brain rhythm. Methods to analyze brain rhythms also include information theoretic measures that are analogously calculated. Certain embodiments of the invention include the use of this digital analysis approach for detection of brain injury. Certain embodiments also include other uses such as sleep pattern analysis, depth of anesthesia analysis, response to cognitive and/or other neurological function and detection of brain injury and recovery processes subsequent to injury. Certain embodiments of the present invention may find use in neurological intensive care units, surgeries, emergency and ambulatory settings, and in neurological examination of the clinical subjects.

Certain embodiments of the present invention solve a problem of interpreting brain rhythms and monitoring neurological trauma. Furthermore, embodiments may provide real-time monitoring of brain state, which is a critical clinical problem. Embodiments include a method to detect and monitor cerebral function and to provide primary brain feature information from the EEG. Thus, certain embodiments provide the ability to quantify changes brought about by multiple variations through a single parameter. One method involves digitization and analysis of EEG rhythms on a computer, description of the EEG rhythms into a mathematical formalism of entropy and information, and computer programs and their implementation in a real-time instrument to provide the interpretation of brain rhythms.

Certain embodiments may act to acquire, collect, display, and store the electrical brain activity from the patient's head within hospitals and clinics. Embodiments may be used during any clinical or surgical event which puts brain's electrophysiological function at risk, such as hypoxia, ischemia, circulatory arrest and trauma. Embodiments may be deployed during clinical events when blood flow to the brain has been compromised and used to continue monitoring neurological sequelae of the brain following the clinical event. Embodiments also may be deployed to detect signs of traumatic brain injury or cerebral pathophysiology, such as cerebral herniation which may be acute injury events, or sequelae of other brain injury. Additionally, embodiments may be used to monitor neurologic status during epilepsy, sleep, coma and/or under administration and management of drugs and/or anesthetics. Embodiments may be used in the critical care area of hospitals and clinics, such as the Cardiac Care Unit, Neurocritical Care Unit, Intensive Care Unit, Operating Rooms, Emergency Rooms, and others.

The entropy measure may be implemented in a variety of mathematical forms. These include the classical form first described by Shannon. Original implementation was formulated in the form of information measure or information content. Subsequently various information measures have been derived. More modern mathematical formulations come from Tsallis and others. Entropy measure is derived in one approach from the digitized signal samples. In other approaches, the entropy measure is derived from the coefficients of any signal processing measure such as Fourier transform and wavelet transform. The inventors also consider time dependent form of entropy, as the biomedical signals such as EEG are time varying and time varying digital signal samples or derived signal coefficients by various methods are useful in arriving at the entropy of the signal. Thus, certain embodiments of the invention relate to diverse forms of entropy and information related measures as applied to the analysis of brain rhythms.

The entropy based analysis methods are described in an expanded manner herein for their use in the interpreting changes in the EEG signals resulting from brain injury. Brain injury may result in a sequence of changes that are highly characteristic, including possible isoelectric line, low frequency rhythms often associated with low entropy levels, high frequency bursting associated with surges in entropy levels, and eventual restoration of brain rhythm at a high entropy state. In addition, the entropy measure is also applicable to analysis of brain rhythms under various other clinical situations and applications. Changes in EEG are evident due to anesthetics. Application of different anesthetic types can alter the EEG signal characteristics and these would be interpreted by the entropy measure. As such a measure of depth of anesthesia can be derived from the analysis of EEG recordings during anesthesia. Similarly, sleep state also provides a characteristic range of signal features which have time, frequency and statistical features. Thus, sleep stage analysis lends itself to be appropriate for entropy based analysis. EEG is an ongoing, real time indicator of cortical function. As such, entropy based analysis of EEG is useful for arriving at a measure of brain's cognitive function, alertness, fatigue and so on. Entropy based analysis is a powerful measure suitable for all normal cortical function assessments and also for pathophysiological measurements. Therefore, certain embodiments include the use of EEG analysis based on entropy related mathematical formulations in a variety of normal and pathophysiological clinical applications.

BRIEF DESCRIPTION OF THE DRAWINGS

Certain embodiments of the invention are described with reference to the accompanying drawings, which, for illustrative purposes, are not necessarily drawn to scale.

FIG. 1 is a schematic illustration of one embodiment of the present invention for brain rhythm acquisition and determination of brain function in a non-invasive manner.

FIG. 2 is a schematic illustration of an EEG acquisition module in accordance with an embodiment of the present invention.

FIG. 3 is a schematic illustration of an EEG processing and analysis module in accordance with an embodiment of the present invention.

FIG. 4 is a schematic illustration of a wireless embodiment of the present invention for brain rhythm acquisition and determination of brain function in a non-invasive manner in accordance with an embodiment of the present invention.

FIG. 5 is a schematic illustration of a wireless EEG acquisition module in accordance with an embodiment of the present invention.

FIG. 6 is a schemative illustration of a wireless EEG processing and analysis module in accordance with an embodiment of the present invention.

FIG. 7 is a schematic illustration of a wireless EEG headcap in accordance with an embodiment of the present invention.

FIG. 8 is a schemative illustration of a remote wireless headcap module in accordance with an embodiment of the present invention.

FIG. 9 is a schematic illustration of a Time Dependent Entropy estimation in accordance with an embodiment of the present invention.

FIG. 10 is a schematic illustration of a Time Dependent Entropy measure of brain function in accordance with an embodiment of the present invention.

FIG. 11 is a schematic illustration of an Entropy measure for irregular electrical events in accordance with an embodiment of the present invention.

FIG. 12 is a schematic illustration of Response and Statistical Characteristics of the Entropy measure in accordance with an embodiment of the present invention.

FIG. 13 is a schematic illustration of the Distance measure of the entropy in accordance with an embodiment of the present invention.

FIG. 14 is a schematic illustration of the Time Dependent Entropy in the EEG analysis module in accordance with an embodiment of the present invention.

FIG. 15 is a schematic illustration of the Subband Wavelet Entropy of brain rhythm to neurological events in accordance with an embodiment of the present invention.

FIG. 16 is a schematic illustration of Subband Wavelet Entropy analysis vs. Subband energy measure in accordance with an embodiment of the present invention.

FIG. 17 displays the residual subband wavelet entropy calculated for an EEG segment with a neurological event in accordance with an embodiment of the present invention.

FIG. 18 is a schematic illustration of the Subband Wavelet Entropy in the EEG analysis module in accordance with an embodiment of the present invention.

DETAILED DESCRIPTION

Certain aspects of the present invention relate to methods for the analysis of brain rhythms. One method described herein relates to a mathematical approach to analyzing brain rhythm based on the concept of information theory and related measures of entropy. In essence, the inventors believe that normal brain rhythm has a highly complex nature, involving varying amplitudes and frequencies, which can be quantitatively described by the measure called entropy. Entropy essentially conveys the sense of randomness or unpredictable aspect of the brain rhythm. The inventors believe that normal brain rhythm has higher entropy. Entropy is related to the measure of information (often measured as number of bits/second). Hence, higher the entropy indicates higher the information rate. Thus, it is believed by the inventors that the normal brain rhythm contains high degree of information as a result of high entropy within the brain rhythm data.

Referring to FIG. 1, the patient 10 is connected to the invention via surface electrodes 12 that contact the patient's head. The EEG (electroencephalographic) signals from the brain are recorded through the use of surface electrodes 12 that are in contact with the patient's head and then transmitted to the acquisition module 14. The acquisition module 14 filters, amplifies and digitizes the EEG signals and sends the digitized signals to the processing and analysis module 16 through a high speed isolated PCI-based interface 18. Through the use of digital signal processing, diagnostic parameters based on the digitized EEG signals are generated and displayed on the processing and analysis module 16.

An embodiment of the EEG Acquisition module 14 is presented in greater detail in FIG. 2. Through the use of complete software control, digital signal pre-processing, and advanced amplifier design, the EEG acquisition module yields high precision signal recording. The electrical signals from a patient's head are first amplified with an ultra-low noise EEG amplifiers 20. This precision EEG amplifier preferably includes high voltage input protection, calibration signal generator, high CMRR ultra-low noise instrumentation amplifier, shield driver, body driver, DC correction circuit, main amplifier and antialiasing low-pass filter. To further improve the module's performance, electrode impedance testing 26 is performed continuously to monitor the integrity of the electrodes contact thus corrections can be made based on the results. Following this, the signals preferably are further conditioned through a software configurable multiplexer 22 and converted into digital signals through the use of a 20 bit sigma-delta converter or other high resolution analog-to digital converter 24. This solution yields to a very high dynamic range which allows the use of variable gain amplifiers to be avoided. The multiplexer, the analog to digital conversion and the impedance test function are preferably controlled by a single chip microcontroller 36. Additionally the single chip microcontroller 36 may perform high pass and low pass digital functions with variable cut-off frequencies and a 60-Hz digital notch filter function. This digital pre-processing of the EEG signals, prior to their transfer to the processing and analysis module, significantly improves the signal quality and the signal to noise ratio. The recorded signals are preferably stored in a local memory 32, which significantly improves the module bandwidth and allows real time operation of the whole system.

Finally, optical isolation circuits 30 are preferably in place to electrically isolate the acquisition module from the processing and analysis module to eliminate the risk of shock to the patient and to reduce the digital noise coming from the host computer. Digital data may be transferred to the EEG processing and analysis module via a high speed PCI interface 34. Calibration, impedance test and normal operation may be remotely controlled, by the host processor through the high speed PCI interface 34. The PCI interface provides a real time connection between the analysis and processing module and the acquisition module and manages the acquisition, calibration and impedance functions of the patient module. The module may be powered by an isolated medical grade DC/DC converter 28.

An embodiment of the EEG Processing and analysis module 16 is presented in greater detail in FIG. 3. A Pentium Single Board Computer Platform 40 may form the basis for the EEG processing and analysis module. Digital signal processing algorithms, real-time operations and real time signals display may be performed through the this Pentium IV-based module which enables high speed performance. This host processor technology provides the computational power necessary for calculating the complex signal processing algorithms that will generate the diagnostic parameters for the overall device. Data from the acquisition module may be brought into the processing and analysis module through the use of the high speed PCI-based Input/Output Module 42. A user may interface with the device through the device's graphical user interface and a flat panel LCD touch screen display 46 or through the user interface controller 44, which may consist of buttons, knobs and/or a keypad, located on the front panel of the processing and analysis module 16. Additionally, data and/or the diagnostic parameters may be outputted into hardcopy form. Data and/or diagnostic parameters are stored in the storage devices 48. The memory 50 is used for temporary data storage needed for the real time signal processing of the EEG signals. The entire Processing and analysis module is powered by a medical grade power supply 54.

FIG. 4 illustrates another embodiment of the present device: a wireless version of the EEG brain rhythm monitor. The device includes a wireless remote EEG Acquisition Module 56 and a wireless EEG Processing and Analysis Module 58. Data between the two modules may be transferred by a wireless method, for, example, BLUETOOTH based wireless telemetry in the ISM radio-frequency band 2402-2480 MHz. The processing and analysis module is preferably designed on a single board computer hardware platform running under a real time operating system. The user interface may be through hardware knobs and switches, which provide basic user control. Advanced user control may be preformed through a touch screen option of the LCD Display.

An embodiment of the wireless remote EEG Acquisition Module 56 is presented in more details in FIG. 5. The electrical signals from a patient's head are first amplified with ultra-low noise EEG amplifiers 60. This precision EEG amplifier preferably includes high voltage input protection, calibration signal generator, high CMRR ultra-low noise instrumentation amplifier, shield driver, body driver, DC correction circuit, main amplifier and anti-aliasing low-pass filter. To further improve the module's performance, electrode impedance testing 66 is performed continuously to monitor the integrity of the electrodes contact thus corrections can be made based on the results. Following this, the signals preferably are further conditioned through a software configurable multiplexer 62 and converted into digital signals through the use of a 20 bit sigma-delta converter or other high resolution analog-to digital converter 64. This solution yields to a very high dynamic range which allows the use of variable gain amplifiers to be avoided. The multiplexer, the analog to digital conversion and the impedance test function are preferably controlled by a single chip microcontroller 72. Additionally the single chip microcontroller 72 may perform high pass and low pass digital functions with variable cut-off frequencies and a 60-Hz digital notch filter function. This digital pre-processing of the EEG signals, prior to their transfer to the processing and analysis module, significantly improves the signal quality and the signal to noise ratio. The recorded signals are preferably stored in a local memory 68, which significantly improves the module bandwidth and allows real time operation of the whole system. The digitized EEG signals as well as control signals are transferred to and from the central unit through the transceiver module 74 and the embedded antenna 70. The module 74 is connected to the single chip microcontroller 72 through a serial communication interface working at high baud rates. The power supply for the module is provided by batteries 78 and the regulator circuit 76.

FIG. 6 shows the overall block diagram of the processing and analysis module 58. Data from the remote acquisition module is transferred through a wireless link, based on a wireless technique, (for example, BLUETOOTH wireless technology), to the processing and analysis module by the transceiver 84 and the embedded antenna 78. The Input/Output Module 80 transfers the data from the Transceiver 84 to the Single Board Computer 82. The Single Board Computer 82 forms the basis for the EEG processing and analysis module 58 which performs digital signal processing algorithms, real-time operations and real time signals display. This host processor technology provides the computational power necessary for calculating the complex signal processing algorithms that will generate the diagnostic parameters for the overall device. A user may interface with the device through the device's graphical user interface and a flat panel LCD touch screen display 88 or through the user interface controller 86, which may consist of buttons, knobs and/or a keypad, located on the front panel of the processing and analysis module 58. Additionally, data and/or the diagnostic parameters may be outputted into hardcopy form. Data and/or diagnostic parameters are stored in the storage devices 90. The memory 92 is used for temporary data storage needed for the real time signal processing of the EEG signals. The entire Processing and analysis module is powered by a medical grade power supply 96.

FIG. 7 illustrates a third embodiment of the present device. In this case the wireless EEG acquisition module 100 is simplified, miniaturized and embedded into an EEG headcap 102. The electronic circuits of the acquisition module 100 may be mounted on a printed circuit board and may be integrated on a flexible or fixed kapton surface. In one alternative configuration, the acquisition module 100 may be surface mounted and may be integrated on a flexible or fixed kapton surface. The EEG headcap 102 may include a transmitter for transmitting a signal to the Processing and analysis module 58. The EEG signals may be digitized and transmitted to the Processing and analysis module 58 through a wireless telemetry technique, (for example, in the ISM radio frequency range) in analog or digital format. In another aspect of this embodiment, one or more electrodes are attached to the EEG headcap in any configuration at any location on the head to obtain one or more cortical EEG readings. As seen in FIG. 7, one example of a configuration includes electrodes distributed in a substantially Y-shaped manner to preferably record cortical EEG readings including one global EEG reading and left and right hemisphere EEG readings. Depending on the specific embodiment, it may be desirable to obtain EEG readings from one or more of a variety of locations of the brain, such as the front, back, left hemisphere, right hemisphere, and global readings. In addition, the EEG headcap may be capable of unipolar and/or bipolar recordings.

The wireless acquisition module 100 is illustrated in greater detail in FIG. 8. A two channel example is shown. The EEG signals may be acquired by high precision differential Delta-Sigma converters 104 and 112. The use of the Delta-Sigma converters allows the elimination of the front end amplification and preprocessing of the EEG signals which significantly simplifies the overall circuit design. An on chip digital antialiasing filter may be used to attenuate signals and noise that are outside the EEG frequency band. This filter avoids the classical problem of the filter settling time which enables simple multiplexing without the need of delay. The differential Delta-Sigma converters offer ultralow noise and simultaneous 50/60 Hz rejection. Highly accurate on-chip oscillator offers high (>110 dB) rejection of AC line frequency interference.

The digitized EEG signals from the Delta-Sigma converters may be continuously transmitted to the Single chip microcontroller 106 through a fast serial peripheral communication interface. The microcontroller 106 controls the channel selection, the acquisition process and the wireless data transmission. The digitized EEG signals may be temporally stored in a internal buffer memory sent in packets to the transceiver 108, which then transfers the signals to the Central module through the embedded antenna 110. The power supply for the module is provided by batteries 114 and the regulator circuit 116.

Certain embodiments also derive quantifiable measures of EEG that can be used to define the neurological events and quantify the evolution of neurological events as observed by the dynamic changes in the EEG. In accordance with certain embodiments, the inventor's have viewed the evolving EEG with a unifying theme of entropy. Entropy measures the general disorder or randomness in a probability distribution or time series. The various measures used such as burst counts, level of bursting/synchronous background activity and interactions between different brain regions during bursting and synchronous activity have a common umbrella or consistent interpretive framework that focuses on the volatility or how unpredictable the EEG signal is. Previous EEG measures can be reinterpreted with a characteristic temporal/spectral entropy formulation. In this fashion both temporal and spectral indicators can be derived to quantify the interplay between the various levels of bursting and synchrony that develops during acute stages of recovery after cardiac arrest. The rationale for certain related embodiments is two-fold: 1) to provide a general, unifying framework that characterizes the entire evolution of EEG response to neurological events, and 2) to provide a methodology suitable for clinical investigation that is robust against subjects, data collection methods and does not require prior or comparative baseline The general characteristics of EEG evolution after brain injury may include (1) silent period, (2) initial burst activity with low amplitude and narrowed spectrum background EEG, (3) fusion of burst activity and the EEG rhythm, and (4) occasionally appearance of seizures. The phenomenon of spectral dispersion (widening of the spectrum) during the recovery stage is directly indicative of the increase in the entropy measure. Besides the spectral changes, the inventors have observed a wide range of variation in the amplitude distribution of EEG which also contribute towards significant increase of the entropy. Large increases in entropy away from monotonous and moribund EEG are evident in a healthy resumption of normal EEG. Generally, speaking as the spectrum widens with healthy recovery the entropy incrementally increases. Likewise as the EEG becomes healthy and robust there are large assortments of amplitudes displayed accompanied by increase of entropy. As the evolving EEG patterns are composed of concomitant episodes of bursting and background rhythms, a reduction in the entropy resulting from the sporadic nature of the bursting component is observed. Through the use of wavelet and sub-band entropy it is possible to pinpoint and localize events in a time-frequency entropy space which offer temporary diversions from general entropic trends. In accordance with certain embodiments, the general process of analysis and interpretation is summarized in the following Tables.

| Entropy state | Normal or uninjured Period | Injury | Early Recovery Phase | Late Recovery Phase |
|---|---|---|---|---|
| Time-dependent Entropy | High entropy indicative of high degree of complexity, statistical fluctuations in the rhythm | Significant drop in entropy concurrent with the absence of signal or signal power | Reduced entropy concomitent with oscillations and bursting as well as seizures | Increasing entropy, with rate or return dependent on outcome (good outcome may have faster better return and vice versa |
| Wavelet or sub-band Entropy | High entropy levels in different sub-bands | Significant drop in all bands | Highly banded structure of sub-band entropy, showing periods of oscillations, bursting, spiking | Return of a very complex, high level of entropy in all sub-bands concurrent with good recovery |

| | | Entropy & Abnormal EEG Characteristics | | | |
|---|---|---|---|---|---|
| EEG | Description | Poor Outcome Summary | Good Outcome Summary | Probable Entropy Interpretation | |
| Burst Occurrence | Burst Frequency or Count | Few Bursts per Minute-Large interburst intervals (IBI) | Large number of bursts per minute | As fusion occurs, there is possibly a lowering of entropy-fewer states that are possible-as a segmented EEG has a greater variety of states to be in. Similarly this must be balanced with the notion that fully fused EEG has perhaps higher volatility than moribund EEG-ambiguity will be solved. The high q factor TMDE gives has higher detection power than other methods | |

-continued

Entropy & Abnormal EEG Characteristics

| EEG | Description | Poor Outcome Summary | Good Outcome Summary | Probable Entropy Interpretation |
| --- | --- | --- | --- | --- |
| Burst Amplitude | How bursty is the EEG?- direct measure of volatility- more volatile EEG has longer basewidth for the bursts | Spiky EEG without uniform amplitude | Low amplitude bursts are difficult to discern from background- pre-fusion EEG | Spiky EEG is more volatile and so has fewer amplitude levels-lower entropy than fused EEG which displays. The MRWE is sensitive enough to discriminate between poor and good outcome |
| Burst Timing | How regularly do bursts occur? | Rhythmic Delta Activity (RDA) and Periodic Bursting with Polyspikes | Fusion of rhythmic bursts into more sporadic background activity | Periodic activity has lower entropy since it occurs with regularity. The MRWE is sensitive enough to discriminate between poor and good outcome |
| Seizures | How rhythmic are the seizures occurring in late recovery EEG? And in long-term EEG monitoring? | Seizures are rapid, hyper-synchronous discharges- periodic in nature | Fusion of the Polyspikes into regular rhythmic activity | Periodic Activity has lower entropy; Though seizures unlike bursts have different time and frequency scale- wavelet entropy will avoid the confusion since different time and frequency scales are observed. Because seizures are of high rhythmicity (almost periodic (one frequency component) TDE detects the presence and measures the duration of them. |

Description of Entropy Algorithms

In the development of the foundations of classical information theory, Khinchin presented a mathematically rigorous proof of a uniqueness theorem for the Shannon entropy based on the additivity law for a composite system in terms of the concept of conditional entropy. Applicants hereby incorporate by reference in its entirety the following publication: Khinchin, A. I. Mathematical Foundations of Information Theory. New York: Dover Publ. 1957.

Suppose the total system can be divided into two sub-systems, A and B, and let $p_{ij}(A,B)$ be the joint probability of finding A and B in their ith and jth microstates, respectively. Then the conditional probability of B given that A is found in its ith state is given by $p_{ij}(B|A) = p_{ij}(A,B)/p_i(A)$, which leads to the Bayes multiplication law $$p_{ij}(A,B) = p_i(A) p_{ij}(B|A), \quad (1)$$

where $p_i(A)$ is the marginal probability distribution: $p_i(A) = \Sigma_j p_{ij}(A,B)$. It should be noted that this form of factorization can always be established in any physical situation. The Shannon entropy (See Shannon, C. E., A mathematical theory of communication. *Bell Syst Tech J* 27: 623-656, 1948, which is hereby incorporated by reference in its entirety) of the composite system is $$S(A, B) = -k_B \sum_{i,j} p_{ij}(A, B) \ln p_{ij}(A, B). \quad (2)$$

Throughout the paper dimensionless units where the Boltzmann constant, $k_B$ is set equal to 1. Thus combining (1) and (2) yields $$S(A,B) = S(A) + S(B|A), \quad (3)$$

where S(B|A) stands for the conditional entropy See Cover, T. and J. Thomas, Elements of Information Theory. New York: Wiley, 1991, p. 12 and p. 224, which are hereby incorporated by reference.

In the particular case when A and B are statistically independent, $p_{ij}(B|A) = p_j(B)$ and from (1) and (2) the additivity law $S(A,B) = S(A) + S(B)$ immediately follows. There is a natural correspondence between the multiplication law and the additivity law:

$$p_{ij}(A,B) = p_i(A) p_{ij}(B|A) \Longleftrightarrow S(A,B) = S(A) + S(B|A), \quad (4)$$

When the above discussion is generalized to any composite system there are theoretical and experimental considerations where systems do not obey the additivity law. (See Tsallis, C., Mendes, R. S., and A. R. Plastino, *The role of constrains within generalized nonextensive statistics.* Physica. A 261: 534-554, 1998, which is hereby incorporated by reference in its entirety. In this respect, a nonextensive generalization of Boltzmann-Gibbs statistical mechanics formulated by Tsallis is better suited to describe such phenomena. (See Tsallis, C., *Possible generalization of Boltmannn-Gibs statistics*, J Statistical Physics, 52: 479-487, 1988, which is hereby incorporated by reference in its entirety.) In this formalism, (offer referred to as nonextensive statistical mechanics), Shannon entropy in (2) is generalized as follows:

$$S_q(A, B) = \frac{1}{1-q} \left\{ \sum_{i,j} [p_{ij}(A, B)]^q - 1 \right\}, \quad (5)$$

where q is a positive parameter. This quantity converges to the Shannon entropy in the limit $q \to 1$. Like the Shannon entropy, it is nonnegative, possesses the definite concavity for all q>0, and is known to satisfy the generalized H-theorem. Nonextensive statistical mechanics has found a lot of physical applications. A standard discussion about the nonadditivity of the Tsallis entropy $S_q(p)$ assumes factorization of the joint probability distribution in (1) ($p_{ij}(A,B)=p_i(A)p_j(B)$). Then, the Tsallis entropy is found to yield the so-called pseudoadditivity $$S_q(A,B)=S_q(A)+S_q(B)+(1-q)S_q(A)S_q(B). \quad (6)$$

Clearly, the additivity holds if and only if $q \to 1$. However, there is a logical difficulty in this discussion. As mentioned above, Tsallis' nonextensivity was devised in order to treat a system with, for example, long-range interactions. On the other hand, physically, "dividing the total system into subsystems" implies that the subsystems are spatially separated in such a way that there is no residual interaction or correlation. If the system is governed by a long-range interaction, the statistical independence can never be realized by any spatial separation since the influence of the interaction persists at all distances. In fact, the probability distribution in nonextensive statistical mechanics does not have a factorizable form even if systems A and B are dynamically independent, and therefore correlation is always induced by nonadditivity of statistics.

Thus, it is clear that the assumption of the factorized joint probability distribution is not physically pertinent for characterizing the nonadditivity of the Tsallis entropy. These considerations naturally lead us to the necessity of defining a conditional entropy associated with the Tsallis entropy.

To overcome the above mentioned logical difficulty and to generalize the correspondence relation in (4) simultaneously, a generalization of Shannon's theorem to Tsallis entropy, (See Santos, R. J. V. da, "Generalization of Shannon's theorem for Tsallis entropy", *J. Math. Phys.* 38: 4104-4107, 1997, which is hereby incorporated by reference in its entirety), composability and generalized (Tsallis) entropy (See Hotta, M. and I. Joichi, "Composability and generalized entropy", *Phys. Lett. A,* 262: 302-309, 1999, which is hereby incorporated by reference in its entirety), and generalizing the Khinchin axioms for the ordinary information theory in a natural way to the nonextensive systems (See Abe, A, "Axioms and uniqueness theorem for Tsallis entropy", *Phys. Lett. A,* 271: 74-79, 2000, which is hereby incorporated by reference in its entirety) may be utilized.

Considering the Tsallis entropy of the conditional probability distribution (See Abe, S. and A. K. Rajagopal, "Nonadditive conditional entropy and its significance for local realism", *Physica. A,* 289: 157-164, 2001, which is hereby incorporated by reference in its entirety), $p_{ij}(A|B)=p_{ij}(A,B)/p_i(A)$ as $$S_q(B|A) = \frac{S_q(A,B) - S_q(A)}{1 + (1-q)S_q(A)}. \quad (7)$$

From this, it is seen that $$S_q(A,B)=S_q(A)+S_q(B|A)+(1-q)S_q(A)S_q(B|A) \quad (8)$$

which is a natural nonaddititive generalization of (3) in view of pseudoadditivity in (6). Therefore the correspondence relation in (4) becomes now $$p_{ij}(A,B)=p_i(A)p_{ij}(B|A) \Longleftrightarrow$$

$$S_q(A,B)=S_q(A)+S_q(B|A)+(1-q)S_q(A)S_q(B|A). \quad (9)$$

This equation coincides with equation (6) of pseudoadditivity when the two systems A and B are independent. In our application the A and B systems represent different sources of brain activity, which are especially distinguishable during brain recovery after ischemia and the data analyzed are the weighed summation of source output traced in the temporal evolution of EEG recordings. In this way the nonadditive Tsallis entropy was formulated according to the Khinchin axioms of information theory and the contradiction between dependency (Bayes law) and long range interaction (nonadditivity) is removed. Embodiments of the present invention includes rationale for a procedure for testing independence between random variables, which the inventors use as a practical tool to analyze the EEG recordings. The results depends upon the entropic index q. It is expected that, for every specific use, better discrimination can be achieved with appropriate ranges of values q.

1) Time dependent entropy—In order to derive an appropriate form of time dependent entropy (TDE) that is sensitive to injury, the inventors present entropy methods to serve as a measure of brain function. Particular forms of entropy are computed from EEG as a method to characterize information content in an EEG signal. Parameters derived from TDE, obtained from application of the Tsallis entropy provide quantitative feedback of brain injury and information regarding cortical activity.

In biomedical signal processing, data are usually modeled with a continuous probability density function (PDF). Usually what is considered, given a signal s(t) and a time window (0,T), is the entropy of the whole curve for the given temporal interval. In this case there are two main approaches. First, the PDF can be approximated by an element of the parameterized set, whose entropy is known in term of the parameters. Second, entropy estimators are based on a priori estimation of underlying PDF's by using kernel methods, autoregressive (AR) modeling of PDF, or histograms. Such an entropy is not very helpful whenever the signal is not stationary and, in case of EEG, nonstationarity results from a combination of spontaneous and burst activities. In such applications, a time-dependent entropy measure is needed.

Let s(t) denote the temporal evolution of the EEG signals. Consider "signal amplitude s(t) vs time" and a discrete-time set of amplitude values $D=\{s(t_k), k=1, 2, \ldots, K\}$. For simplicity, from now on the notation $s(k)=s(t_k)$ is used.

In order to compute the pertinent probability distribution, the amplitude domain D is partitioned into L equidistant boxes or disjoint amplitude intervals, $I_l (l=1, 2, \ldots, L)$ covering the space between maximum and minimum amplitude of the respective EEG segment. In particular if $$s_o=\min[D]=\min\{s(k),k=1,2,\ldots,K\},$$

$$s_L=\max[D]=\max\{s(k),k=1,2,\ldots,K\} \text{ and}$$

$$s_o<s_1<s_2 \ldots <s_L$$

then there is a set of boxes or disjoint intervals $\{I_l=[s_{l-1},s_l], l=1, 2 \ldots, L\}$ such that $$D = \bigcup_{l=1}^{L} I_l.$$

A sliding temporal window W depending on two parameters including the size w (an even number) and the sliding factor Δ is defined. A sliding window of the data is defined according to $$W(m;w;\Delta)=\{s(k), k=1+m\Delta, \ldots, w+m\Delta\}, m=0,1,2 \ldots, M$$

where Δ and w are selected such that w<=K, (K−w)/Δ∈N and M=(K−w)/Δ. The center of window W is s(w/2+mΔ) and m controls the consequential time displacement from the first (m=0) until the last window (m=(K−w)/Δ)). FIG. 9 is a Time Dependent Entropy estimation paradigm. The 1024 data points signal is partitioned to 10 disjoint amplitude intervals. The window size is w=128 and it slides every Δ=32 points.

The probability that the signal s(k)∈W(m;w;Δ) belongs to the interval $I_l$ is denoted by $P^m(I_l)$. This probability is the ratio between the number of s(k)-values of W(m;w;Δ) found within $I_l$ and the total number of s(k)-values in W(m;w;Δ).

The Shannon entropy measure associated with this probability is $$SE(m) = -\sum_{1}^{L} P^m(I_l) \ln P^m(I_l),$$

while the corresponding Renyi and Tsallis entropy measure is $$RE(n) = -(q-1)^{-1} \sum_{i=l}^{M} \ln P^n(I_i)$$

$$TE(m) = -(q-1)^{-1} \sum_{1}^{L} [P^m(I_l)^q - P^m(I_l)]$$

Step-by step description of the of the Time Dependent Entropy algorithm:
1. To calibrate the algorithm (for each specific object, the EEG amplitude might not be within the same range due to the difference of the contact between the electrode and the scalp and the physiological state of the object and etc.), a baseline EEG segment signal (>3 min) is used to get the partitioning for entropy calculation. Generally an amplitude interval which covers the 99% baselines samples is preferably used as the reference interval for partitioning.
2. Selection of q factor—non-extensiveness parameter—dependent on whether or not it is desired to observe phenomena that evolve slowly over time or change rapidly from observation window to observation window. What makes the localized multi-resolution entropy measure unique is this q-parameter. By judiciously choosing the value of the control parameter, the information rate can either focus on to long range rhythm or to short and abrupt changes (bursts or spikes).
3. Selecting the partition number L for estimate the histogram based probability distribution. The L partition are applied to the reference amplitude interval got in (1). During the brain injury, the amplitude distribution is clearly different from that of baseline, which will be accordingly illustrated by the entropy.
4. Move sliding window of N pts. through time series window by window. The EEG could be explored by the TDE evolution real time.

Localized or Time Multi-resolution Dependent Entropy (TMDE): Since wavelets have interesting localization properties in the time frequency plane, a multiresolution Tsallis entropy is derived to characterize the local state changes such as burst patterns or epileptiform seizures as expected during the recovery process. The wavelet coefficients corresponding to the level j are $D_j = \{d_j(k), k=1, \ldots, 5\}$.

Instead of raw EEG data, if the wavelet coefficients are the input of the algorithm for the TDE, then we will have a Localized or Time Multiresolution Dependent Entropy (TMDE) method.

This allows for a frequency selective entropy method as a measure of events such as spikes, bursts, and fusion of discharges during recovery—

To account for the time-varying signal statistics, localized in different frequency bands, the time-frequency distribution for estimating the probability density function in the definition of entropy is considered. In this approach, the probability density function is replaced by the coefficients C(t,f) of a given time-frequency representation (TFR). Since several TFRs can achieve negative values, the use of the more classical Renyi entropy with an order parameter q has been applied to describing the complexity of EEG signals.

$$H_q(\Delta t) = \frac{1}{1-q} \log_2 \left( \int \int \left( \frac{C(t,f)}{\int\int C(t,f)} \right)^q \right)$$

The passage from the Shannon entropy to the class of order selective entropy involves only the relaxation of the mean value property from an arithmetic to an exponential mean and thus in practice, $H_q$ behaves much like H. In situations where the distributions representing the probability density function changes rapidly, Shannon entropy fails to provide information about the localized changes occurring in the signal. To deal with such cases, a non-extensive generalization of Shannon entropy may be used. This formalism is based on a non-logarithmic entropy $$H_q(\Delta t) = \frac{1 - \int\int \left[ \frac{C(t,f)}{\int\int C(t,f)} \right]^q}{q-1}$$

For q 1 Tsallis entropy coincides with Shannon entropy. By judiciously choosing the value of q, it is possible to localize the features of the original distribution $\{p_i\}$.

In FIG. 10, the TDE measures provide analysis, interpretation, and feedback on the evolution of neurological events. In this case the entropy measure drops due to a mild ischemic event 113 and recovers to the original level in a short time period. More severe ischemic brain injury 114 & 115 causes drops in entropy and require more time to return to original entropy levels. This entropy measure can be used to quantify and observe the evolution of brain function due to neurological events.

In FIG. 11, the raw EEG sample with EEG events displayed in 111. The TDE measure is effective in detecting these electrical events 112 including bursts, burst and burst suppression patterns, discharges, irregular EEG activity or patterns, spikes, and sleep spindles. The entropy measure can be used to detect neurological events and/or electrical events in the EEG signal.

In FIG. 12, the compressed raw EEG is displayed with three raw EEG segments A, C, and E. The statistical characteristics of the entropy measure are indicated in the graph with the mean entropy measure on the left axis and the standard deviation on the right axis. The physiological phases are segmented and quantified clearly by the mean entropy. Phases (A)~(E) are: (A) the baseline (0-15 min); (B) phase after ischemic brain event (15~34 min); (C) early recovery, (35~80 min); (D) middle recovery, (80~160 min); (E) late recovery, (after 160 min). The standard deviation of the entropy measure reveals the information of burst activity as indicated by the rise in C during which the raw EEG segments shows evidence of bursting.

Entropy measures can also be represented as a distance measures. The relative entropy or Kullback Leibler distance between two probability functions p(x) and q(x) is defined as $$D(p \| q) = \sum_{x_i} p(x_i) \ln \frac{p(x_i)}{q(x_i)}$$

In this case entropy measures derived from EEG during the pre-event (baseline) are compared with EEG during neurological event.

In FIG. 13, an example of the relative entropy measure is displayed with baseline 130, beginning of an neurological event (for example hypoxia) 131, further neurological events (asphyxia and recovery) 132, and after the events (recovery) 133. The distance from the baseline indicates the change and evolution of brain function during the course of neurological sequelae. The relative entropy method is applicable to other measures including TDE, localized or time multi-resolution dependent entropy, subband wavelet entropy, multi-resolution wavelet entropy, or residual entropy.

The flowchart presented in FIG. 14 describes a method for time dependent entropy estimation based on sliding temporal window approach by the EEG analysis module. The raw sampled EEG signals are continuously acquired and stored in the Acquisition Buffer. The Length of the acquisition buffer is set equal to the sliding step size Δ (142). This Buffer is updated at every iteration and stores the Δ most recent acquired samples. In step 143 the program sets the baseline segment length—n. The baseline segment (example 3 or 4 min of raw EEG data) is needed in order to evaluate the amplitude interval (maximum and minimum boundaries) in which the partitioning will be performed. The program continues by checking whether the Acquisition Buffer is filled (144) and if it is, stores the data in the input data array S (145). In step 146 the program checks whether the number of samples contained in the input data array is equal to the sliding window length w and if so performs another check whether the baseline flag is set (7). If this flag is not set (initial conditions) the maximum and minimum amplitudes in the current window are located and stored (148). The program continues this loop until the end of the baseline length is reached (n=0). After this initial period the Baseline flag is set (152) to ensure that the initial configuration steps are not performed again. In step 153 the program evaluates the maximum and the minimum amplitude values stored during the baseline recording and sets the amplitude domain D. This amplitude domain D covers 99% of the maximum and minimum amplitude values previously stored. This is done for avoiding the effects of transient low frequency artifact that might occur in EEG recording. In step 154 the amplitude domain D is partitioned in L amplitude sub-intervals (bins). At this point of the program the initial configurations and calibrations are completed. In step 155 the program continues by computing the histogram of the input array within L amplitude sub-intervals. The histogram is obtained by counting the number of times the elements in the input array fall in the $x^{th}$ amplitude sub-interval. The results are stored in the Histogram array P. In the next step 156 the histogram array is used for the probability distribution estimation, which is calculated as the ratio between the histogram value P(x) for $x^{th}$ amplitude sub-interval and the total number of histogram values within all L amplitude intervals. In step 157 the probability distribution results are used for Entropy index calculation. After storing and displaying the Entropy index 158 the input data array S is shifted by Δ elements (150) and the program continues by acquiring the next Δ samples.

2) Multi-Resolution Wavelet Entropy (MRWE) or Subband Wavelet Entropy—

The conventional definition of entropy (Shannon entropy) is described in terms of the temporal distribution of signal energy in a given time window. The distribution of energy in a specified number of bins (n) is described in terms of the probabilities in signal space $\{p_i\}$ using which the entropy of the signal in a given time window (Δt) is defined as $$H(\Delta t) = -\sum_n p_i \times \log(p_i)$$

An efficient estimator for the density function usually requires either several samples of the process or strong assumptions about the studies process. To account for the non-stationarities in the EEG following resuscitation and gradual recovery, the time-frequency distribution for the definition of entropy is considered. In this approach, the probability density function is replaced by the coefficients C(t,f) of a given time-frequency representation (TFR) of the signal. The extended definition is given by $$H(\Delta t) = -\sum_t \sum_f C(t, f) \log C(t, f)$$

Since several TFRs can achieve negative values, the use of the more classical Shannon information is modified to have an order parameter q as:

$$H_q(\Delta t) = \frac{1 - \sum_{t,f} [C(t, f)]^q}{q - 1}$$

The passage from the Shannon entropy to the class of order selective entropy involves only the relaxation of the mean value property from an arithmetic to an exponential mean and thus in practice, $H_q$ behaves much like H. In situations where the distributions representing the probability density function changes rapidly, the parameter q acts like a spatial filter. By judiciously choosing the value of q, it is possible to localize the features of the original distribution $\{p_i\}$.

Alternatives and advancement—The rationale behind substituting the density function P by the coefficients C(t,f) of the TFR is very appealing and introduces an elegant way of exploring the values of the control parameter to be used in the estimates. The peaky TFRs of signals comprised of a small numbers of elementary components (organized signals) would yield small entropy values, while the diffuse TFRs of more complex signals would yield large entropy values. This leads to an issue as to the choice of TFR to obtain the most accurate estimates of entropy for a given data set. In practice, the inventors believe the best estimates are obtained with the TFR which is better in separating the elementary components The problem of rapidly changing signal statistic is addressed by using the optimal time-frequency representation using different scales of wavelet decomposition. By using sub-bands which are mutually uncorrelated, the signals can be made to be statistically independent in addition to being spectrally non-overlapping as in the clinical definition of the EEG bands. Using the discrete wavelet transform, it would be possible to achieve an optimal decomposition of the EEG into sub-bands that are mutually orthogonal and statistically independent. By using a sampling frequency of 250 Hz and choosing five levels of decomposition, the sub-bands can be made identical to the clinical bands of interest.

The TFR based on Fourier analysis suffers from a problem because the spectral selection concept is based on a sinusoidal representation, which has an infinite extent in the basis function. As a result, activity with sharp variations in amplitude, phase and frequency such as the burst activities present in the EEG after injury cannot be well resolved. The basis functions of the wavelet transform are able to represent signal features locally and adapt to slow and fast variations of the signal. The wavelets used in our method should be able to represent the EEG burst activity.

The wavelet decomposition for a given EEG signal s(t) is obtained as $$s(t) = \sum_{j=-\infty}^{\infty} \sum_{k=-\infty}^{\infty} d_j(k)\psi(2^{-j}t - k)$$

At each level j, the series s(t) has the property of complete oscillation, which makes the decomposition useful in situation where the signal statistic varies with time. Because of the sensitivity of a complex system with its initial conditions, determined by the baseline period), there is a change in the available information about the states of the system in the event of injury. This change can be thought of as creation of information if it is considered that two initial conditions evolve into distinguishable states after a finite time. To characterize the time varying nature of these distinguishable states, wavelet decomposition can be performed over short windows each of 1 sec duration or less. It is assumed that the signal states are slow varying so that for a given sub-band, there is a strong correlation between the states represented by the wavelet coefficients at different locations within a time window. The initial part of the algorithm focuses on characterizing a unique measure of the states in terms of the sub-band entropy function. Unfortunately, it may not be possible to be able to directly measure this entropy by nonintrusive methods. Thus, approximating this entropy at different scales using a multi resolution approach is done. The global entropy at scale j, is defined by the equation $$H_j = -\frac{\sum_k |d_j(k)|}{\sum_j \sum_k |d_j(k)|} \times \log\left(\frac{\sum_k |d_j(k)|}{\sum_j \sum_k |d_j(k)|}\right)$$

Entropy based segmentation—The global entropy measure derived in the previous section will then be used to derive a delineation function for the purpose of segmenting the EEG into different phases of recovery. In general, the different phases are delineated by segmenting the information flow as detected using the local entropy function. The delineation function is obtained by adding the weighted sum of the sub-band entropy functions using $$\Psi(t) = \sum_j w_j(t) H_{qj}(t)$$

where $w_j(t)$ is the relative time-dependent sub-band energy density defined as the ratio of sub-band energy in the j'th sub-band to the sum of the energy contributions in all the sub-bands. The observations on the energy density and the time-dependent entropy are independent Gaussian variables in the limiting case. The time-instants of change of the delineation function is then detected by a change in the mean level of the sequence given by the sum of the weighted sub-band entropy values. To detect these changes or jumps in the delineation function, the finite memory effects are considered and a triangular filter with impulse response of triangular form is used to smooth out the changes in the mean levels. The filtered values of the delineation function is obtained using $$\nabla \Psi(t) = \left| \sum_{i=0}^{p-1} \Psi(t-i) - \sum_{i=p}^{2p-1} \Psi(t-i) \right|$$

If the two half windows have the same value for the delineation function, the resulting jump will be zero and if the window is located around a segment boundary, the jump function will take a large positive value.

To compute the subband wavelet entropy, the EEG signal is first divided into windows each of 1 min duration. The wavelet decomposition for a given EEG signal s(t) is obtained by:

$$s(t) = \sum_{j=1}^{N} \sum_k C_j(k) \psi(2^{-j}t - k) = \sum_j r_j(t)$$

Where the wavelet coefficients $C_j(k)$ can be interpreted as the local residual errors between successive signal approximations at scales j and j+1, and $r_j(t)$ is the residual signal at scale j. Each subband contains the information of the signal s(t) corresponding to the frequencies $2^{j-1}\omega_s \leq |\omega| \leq 2^j \omega_s$. The subband wavelet entropy is now defined in terms of the relative wavelet energy (RWE) of the wavelet coefficients. Due to the orthornormal nature of the basis functions used, the concept of energy is linked with the usual notions from Fourier theory. The energy at each resolution level j=1, . . . , N, will be the energy of the detail signal.

$$E_j = \|r_j\|^2 = \sum_k |C_j(k)|^2$$

The total signal energy is obtained as in $$E_{total} = \sum_j E_j$$

Then, the normalized values, which represent the RWE are expressed as in $$p_j = \frac{E_j}{E_{total}}$$

Since $$\sum_j p_j = 1,$$

the distribution $\{p_j\}$ can be considered as a time-scale density.

For each of these windows, the five levels wavelet decomposition is computed using the multiresolution decomposition algorithm. The energy of each wavelet resolution is then calculated followed by calculating the total energy of the wavelet coefficients at all resolutions. The relative wavelet energy is determined for each resolution and finally, the entropy of each resolution level is computed. The entropy values are smoothed using a first order median filter before displaying the subband entropy in the form of a "checkerboard" plot of gray levels. Each cell in the plot has a gray level resulting from bilinear interpolation of the neighboring four values of entropy. The smallest and largest elements of the resulting vector of entropy values are assigned the 0 and 1 values of the gray levels respectively.

FIG. 15 displays the subband wavelet entropy calculated for an EEG segment with a neurological event. The subband wavelet entropy response consists of delta, theta, alpha, beta, gamma subband 162-166, where the subband wavelet entropy will exhibit different responses due to the neurological event. In the case of ischemic brain injury, the subband wavelet entropy drops and recovers differently in each subband. Usually, higher frequency bands (gamma) return to normal entropy faster than slower frequencies (delta). The response of subband wavelet entropy may be used to detect and interpret different neurological events (for example, cortical injury, bursts, spikes, spindles) and augment standard clinical subband energy calculations.

FIG. 16 shows the normalized gray coded segments obtained using the MRWE and relative powers of a simulated EEG signal. A gray bar display has been developed to describe the entropy trends in different subbands. Black and white represent the lowest and the highest levels of entropy, respectively. The injury and silence periods are represented by black. The recovery in different bands is judged by comparing the closeness between the gray level of the baseline and the different phases of recovery.

The gray coded segmentation using MRWE shows the graded patterns of recovery in different bands. In our simulation, for example, the low frequency bands are recovering faster than the high frequency bands. In comparison, the segmentation using the relative powers of traditional clinical subbands fail to reveal the graded variations in early recovery in each subband. The bands obtained using MRWE will be used for a more detailed analysis and interpretation of the cortical EEG rhythms and to help identify the dynamic patterns of rhythmic bursts in the thalamic and cortical neurons.

The Residual Entropy

Residual entropy is considered to be a measure of deviation from the mean entropy of the background EEG. It is based on the information quantity of entropy. Since the background EEG is quasi-gaussian and bursting is non-gaussian, residual entropy is used to measure the degree of bursting activity. The residual entropy is defined as $$J(x) = H(x) - E[H(x)]$$

Where E denotes the expectation operator and H is the entropy of the random variable x.

Sub-Band Wavelet Entropy and Residual Entropy

To account for the non-stationarities in each frequency band, the entropy is defined using an optimal time-frequency representation. The time-frequency representation based on Fourier analysis suffers from a significant problem because the spectral selection concept is based on a sinusoidal representation, which has an infinite extent in the basis function. The basis functions of the wavelet transform are able to represent signal features locally and adapt to slow (such as background EEG) and fast variations (such as bursting components)) of the signal. Other requirements are that the wavelet should satisfy the finite support constraint, differentiability to reconstruct smooth changes in the signal symmetry to avoid phase distortions.

Substituting the density function P by the wavelet coefficients permits one to explore the values of the control parameter to be used in the estimation of Residual Entropy of the different clinical bands. The peaky wavelet coefficients obtained from the discrete wavelet decomposition of EEGs comprised of a small numbers of more organized rhythm components would yield small entropy values, while the diffuse nature of more complex rhythms would yield large entropy values. This leads to a question as to the choice of the type of wavelet basis to obtain the most accurate estimates of entropy for a given data set. From simulated examples, the inventors have observed that the best estimates may be obtained by using the orthogonal wavelet basis.

Let s(t) represent a Gaussian continuous time EEG signal with zero mean, $E[s]=0$ and variance $E[s^2]=\sigma^2$. If $\psi(t) \in L^2(\Re)$ is a basic mother wavelet function, then the wavelet transform of s(t) is defined as the convolution between the EEG signal and the wavelet functions $\psi_{a,b}$ (See Metin Akay, "Time Frequency and Wavelets in Biomedical Signal Processing", IEEE Press, New York, 1996, which is hereby incorporated by reference in its entirety.)

$$WT\{s(t); a, b\} = \frac{1}{\sqrt{|a|}} \int_{-\infty}^{\infty} s(t) \psi_{a,b}^* \left( \frac{t-b}{a} \right) dt$$

where a,b∈ℜ, α≠0 are the scale and translation parameters respectively, t is the time and the asterisk stands for complex conjugation. If $a=2^j$ and $b=k2^j$, then the discrete subband wavelet transform $y_j(k)$ of a sampled EEG sequence $s=[s(1), s(2), \ldots, s(N)]^T$, is given by:

$$DTWT\{s(n); 2^j, k2^j\} = y_j(k) = \sum_n s(n) h_j^*(n - 2^j k) \; j, k \in Z$$

where j represents the wavelet resolution level and $h_j(n-2^j k)$ are the analysis wavelets which are discrete equivalent to the $2^{-j/2} \psi[2^{-j}(t-2^j k)]$ Since the response of a linear system to a Gaussian process is also a Gaussian process, then at each resolution level, j, the wavelet coefficients sequence, $y_j(k)$ is also a Gaussian with $E[y_j]=0$ and variance $E[y_j^2]=\sigma_j^2$. If $h_j(n)$ is finite in length, then the variance of $y_j(k)$ my be expressed in terms of the autocorrelation matrix, $R_s$ of EEG sequence and the wavelet analysis vector coefficients h as follows (See M. Hayes, "Statistical Digital Signal Processing and Modeling", John Wiley & Sons, Inc., New York. 1996, which is hereby incorporated by reference in its entirety):

$$E[y_j^2] = h_j^H R_s h_j$$

The entropy of a zero mean Gaussian signal with variance=$\sigma^2$ is given by:

$$H = \frac{1}{2} \log(2\pi e \sigma^2)$$

(See A. Papoulis, 'Probability, Random Variables, and Stochastic Processes", McGraw-Hill Book Company, Auckland, 1984, which is hereby incorporated by reference in its entirety.) For the discrete Gaussian wavelet coefficients sequence, $y_j$, $H_j$ is:

$$H_j = \frac{1}{2} (\log(2\pi e) + \log(h_j^H R_s h_j))$$

For a stationary process, the average entropy of consecutive temporal wavelet coefficient s windows is defined as:

$$\overline{H}_j = E[H_j] = \frac{1}{2} (\log(2\pi e) + \log(h_j^H E[R_s] h_j))$$

However, if the statistics of the EEG signal change as a function of time, then the instantaneous residual entropy at each wavelet coefficients temporal window is:

$$\Delta H_j = \frac{1}{2} (\log(h_j^H R_s h) - \log(h_j^H E[R_s] h)) = \frac{1}{2} \log \left( \frac{h_j^H R_s h_j}{h_j^H E[R_s] h_j} \right)$$

Since the wavelet analysis functions are deterministic and invariant over time, then the variations of the residual entropy depends only on the temporal variations of the wavelet coefficients window.

Each level contains the information of the signal s(t) corresponding to the frequencies $2^{j-1} \omega_s \leq |\omega| \leq 2^j \omega_s$. The biorthogonal wavelet was selected with order that resulted in the least oscillations at the course levels due to spiking.

The subband wavelet entropy (SWE) is now defined in terms of the Relative Wavelet Energy (RWE) of the wavelet coefficients. Due to the orthornormal nature of the basis functions used, the concept of energy is linked with the usual notions from Fourier theory. The energy at each resolution level j=1, . . . ,N, will be the energy of the detail signal $$E_j = \|r_j\|^2 = \sum_k |C_j(k)|^2$$

and the total signal energy is obtained as $$E_{total} = \sum_j E_j$$

Then, the normalized values, which represent the RWE is expressed as:

$$p_j = \frac{E_j}{E_{total}}$$

Since $$\sum_j p_j = 1,$$

the distribution $\{p_j\}$ can be considered as a time-frequency-scale density. The SWE for the j'th level is obtained by inserting the value of the above time-frequency-scale density into Eq. (1). This provides a suitable tool for characterizing the frequency specific variations projected onto the time scale. Larger the number of levels around a frequency, the higher the resolution of the density function. At each level j, the series s(t) has the property of complete oscillation, which makes the decomposition useful in situation where the frequency characteristics vary with time. To characterize the time varying nature of these distinguishable states, wavelet decomposition can be performed over short windows each of 1 min duration or less. It is assumed that the signal states are slow varying so that for a given clinical band of interest, there is a strong correlation between the states represented by the wavelet coefficients at different locations within a time window. To enhance the detection of the coherent peaks in the entropy profile, the Residual Entropy of the Wavelet coefficients (RSWE) is defined as $$J_j(y_j) = H(y_j) - E[H(y_j)]$$

For an EEG signal frame of T sec, sliding windows are defined, each of width Δ. The mean entropy of the frame is the mean of the SWEs of the sliding windows. Denoting the wavelet coefficients of the m'th window in the n'th frame as $y_j^{m,n}$, the mean entropy of the m'th frame is $$E[H(y_j^n)] = \frac{1}{M} \sum_{m=1}^{M} H(y_j^{n,m})$$

The residual entropy of the n'th frame is then defined by $$J_j^{m,n} = H(y_j^{n,m}) - E[H(y_j^n)]$$

The Residual Subband Wavelet Entropy (RSWE) is then defined as the difference between the time-varying entropy and the slowly varying mean entropy. The time-varying changes in the SWE may be attributable to the combined effects of bursting components and the slowly varying background activity in each level of decomposition. FIG. 17 displays the residual subband wavelet entropy calculated for an EEG segment with a neurological event. The residual subband wavelet entropy response consists of delta, theta, alpha, beta, gamma, where residual subband wavelet entropy will exhibit different responses due to the neurological event. In the case of ischemic brain injury, the residual subband wavelet entropy rises and recovers differently in each subband. The response of residual subband wavelet entropy may be used to detect and interpret different neurological events (for example, cortical injury, bursts, spikes, spindles) and augment standard clinical subband energy calculations. The RSWE may be used to determine coherent synchrony and bursting patterns in the subbands. The residual entropy methods are applicable to other entropy measures including TDE, localized or time multi-resolution dependent entropy, multi-resolution wavelet entropy, or relative entropy.

The flowchart presented in FIG. 18 describes a method for wavelet entropy estimation based on a sliding temporal window approach by the EEG analysis module. The raw sampled EEG signals are continuously acquired and stored in the Acquisition Buffer. The Length of the acquisition buffer is set equal to the sliding step size Δ (172). This Buffer is updated at every iteration and stores the Δ most recent acquired samples. In step 173 the program checks whether the Acquisition Buffer is filled and if it is, stores the data in the input data array S (174). The program continues by checking whether the number of samples contained in the input data array S is equal to the sliding window length w (175) and if so computes the n levels wavelet transformation—WT (176). This transformation is obtained by decomposing the current EEG segment contained in the input data array S into n discrete bands using the standard discrete wavelet transform algorithm or Biquadratic spline wavelet transform algorithm. In step 178 the program continues by estimating the energy of the wavelet coefficients in each level of decomposition—$E_j$. The energy loop is incremented (180-181) until the energies from all the levels are added up (179). The total energy $E_T$ is computed by squaring and adding the wavelet coefficients. The total energy values are then stored in a buffer. The program then (183) begins to compute the relative wavelet energy (RWE) in each level of decomposition ($E_{rel}$). The relative wavelet energy is computed by dividing the energy of wavelet coefficients in each level of decomposition $E_j$ by the total energy of the wavelet coefficients ($E_T$). The loop continues by estimating the entropy levels in each level of decomposition (184). Each time the loop executes, it accesses the total energy stored in the buffer from the previous loop. After storing and displaying the Entropy index 186 the input data array S is shifted by Δ samples (187) and the program continues by acquiring the next Δ samples.

Certain examples of embodiments of the present invention are described below. Various features described below in connection with specific examples may be applied to the other examples.

A first method example includes monitoring the brain for evidence of a neurological event using a plurality of electrodes on a patient's head, electronic instruments, a computer to record information and entropy algorithms to analyze brain rhythm information. The entropy algorithms may include a measure such as TDE, localized or time multi-resolution dependent entropy, multi-resolution wavelet entropy, subband wavelet entropy, relative entropy (relative TDE, relative localized or time multi-resolution dependent entropy, relative multi-resolution wavelet entropy, relative subband wavelet entropy), or residual entropy (residual TDE, residual localized or time multi-resolution dependent entropy, residual multi-resolution wavelet entropy, residual subband wavelet entropy). It should be understood that the mathematical algorithm may utilize more than one entropy measure.

The first method example may include detecting the neurological event by sensing the electroencephalogram signal and determining the occurrence of neurological injury based on the electroencephalogram signal.

The first method example may include detecting the neurological event using a tissue impedance sensor connected to the subject, wherein the information gathered by the sensor permits the distinguishing of a neurological event such as a neurological injury condition from a non-neurological injury condition.

The first method example may include detecting neurological event by a method including using electroencephalogram signals, and analyzing the signals using an analysis selected from the group consisting of (1) an electroencephalogram waveform analysis using time-domain signal analysis methods, (2) an electroencephalogram waveform analysis using a frequency domain method such as FFT and filtering, (3) an electroencephalogram waveform analysis using a combined time and frequency analysis method, (4) an electroencephalogram waveform analysis using entropy analysis methods, (5) an electroencephalogram waveform analysis using wavelet analysis methods, and (6) an electroencephalogram waveform analysis using information theoretic analysis.

The first method example may include analyzing the electroencephalogram signal using a frequency domain method selected from the group consisting of fast Fourier transform and filtering.

The first method example may include analyzing the electroencephalogram signal using a combined time and frequency analysis selected from the group consisting of joint time frequency distributions, time dependent entropy analysis, multiresolution time dependent entropy analysis, subband wavelet analysis, and subband wavelet entropy analysis.

A second method example includes embodiments for monitoring the brain of a subject for evidence of a neurological event using entropy methods. The method example includes positioning at least one sensor on the head of the subject, the sensor being electrically connected to a device include circuitry and a microprocessor, and determining whether a neurological event has occurred using entropy methods.

A number of aspects which may be used in embodiments of the second method example are discussed below.

The second method example may include positioning a plurality of sensors in or on the head of the subject, in one or more locations in or on the head of the subject. It may be possible to position sensors directly on the brain in certain embodiments.

The second method example may include positioning at least one sensor to provide electrical access to cutaneous regions in the vicinity of the brain.

The second method example may include at least one sensor selected from the group consisting of electrical, mechanical, hemodynamic, conducting polymer electrodes.

The second method example may comprise the microprocessor including at least one entropy algorithm for interpreting a signal generated by the at least one sensor and determining whether a neurological event (for example, an injury) has occurred.

The second method may include transmitting at least one signal through at least one of the sensors to the circuitry, amplifying the signal, filtering the signal, and converting the signal from an analog signal to a digital signal.

The second method may including transmitting a plurality of signals from a plurality of sensors to the circuitry, and feeding the signals to a multiplexer, converting the signal from an analog signal to a digital signal, and delivering the signal to the microprocessor.

A third example includes method embodiments for monitoring a brain of a subject for evidence of a neurological event, including a device including a plurality of leads positioned on the head and connected to circuitry positioned on the subject. The device may be designed to include wireless transmission capabilities to connect the device to an apparatus adapted to determine whether a neurological event has occurred using entropy algorithms to analyze the brain rhythm information.

Additional examples include methods for monitoring the brain for specific neurological events using entropy methods to analyze the brain rhythm information. Such events may include, for example, an epileptic seizure, the depth (and effects) of anethesia, sleep and sleep staging, cognitive functions (e.g., wakefulness, alertness, function, and normal neurological functions) and brain injury (e.g. ischemia, hypoxia, asphyxia), burst and burst suppression patterns, discharges, spikes, spindles, irregular electrical event in the EEG), cortical function and response to neurological therapies and/or molecular agents including drugs.

In addition, various embodiments may be used in a variety of settings in and out of a hospital, such as monitoring the brain in neurological intensive care units, monitoring the brain in the operating room, monitoring the brain in ambulatory subjects, monitoring the brain during clinical neurological examinations, using one or more electrodes on the patient's head, electronics instruments and a computer to record, and an entropy algorithm to analyze the brain rhythm.

In addition, monitoring brain rhythms may be carried out in various embodiments through the use of EEG amplifiers, computer-based data acquisition and signal processing, electrical instruments such as microprocessors, digital signal processors, storage devices, computers, monitors, work stations, etc., for acquiring, recording and displaying EEG signals and/or providing analysis interpretation of brain rhythms using entropy methods. In addition, monitoring the brain rhythms may include using ambulatory EEG, monitoring EEG using a plurality of electrodes such as multi-channel recordings, electrode arrays on the scalp and in/or other position of the head.

It will, of course, be understood that modifications of the present invention, in its various aspects, will be apparent to those skilled in the art. Additional embodiments are possible, their specific features depending upon the particular application.

What is claimed:

1. A method of monitoring neurological function, comprising:

acquiring electroencephalogram signals from a subject; and processing and analyzing data from the electroencephalogram signals using at least one entropy method selected from the group consisting of: Shannon entropy, Tsallis entropy, Renyi entropy, time dependent entropy, time multi-resolution dependent entropy, relative time dependent entropy, relative time multi-resolution dependent entropy, residual time dependent entropy, residual time multi-resolution dependent entropy, subband wavelet entropy, multi-resolution wavelet entropy, relative subband wavelet entropy, relative multi-resolution wavelet entropy, residual subband wavelet entropy, and residual multi-resolution wavelet entropy;

wherein the processing and analyzing data includes analyzing at least one electroencephalogram waveform segment, wherein the at least one electroencephalogram waveform segment comprises a plurality of data points from the electroencephalogram signal; and wherein the processing and analyzing data further comprises calculating the maximum and minimum amplitude value of the data points from the at least one electroencephalogram waveform segment and determining an amplitude domain with upper and lower amplitude boundaries based on statistical analysis and processing of the maximum and minimum amplitude values of the at least one electroencephalogram waveform segment.

2. A method as in claim 1, wherein the processing and analyzing data further comprises determining sub-intervals partitioned from the amplitude domain, calculating the occurrence of data points from the at least one electroencephalogram waveform segment in the sub-intervals, and tabulating the calculated information into a statistical array.

3. A method as in claim 1, wherein the statistical array comprises a histogram.

4. A method as in claim 2, wherein the processing and analyzing data further comprises deriving a probability calculation with statistical methods for determining the occurrence of data points from the at least one electroencephalogram waveform segment in the sub-intervals.

5. A method as in claim 2, wherein the processing and analyzing data further comprises calculating entropy values with the at least one entropy method using the probability calculation for the occurrence of data points from the at least one electroencephalogram waveform segment in the sub-intervals.

6. A method as in claim 5, further comprising storing and displaying the entropy values.

* * * * *

UNITED STATES PATENT AND TRADEMARK OFFICE
CERTIFICATE OF CORRECTION

PATENT NO. : 7,299,088 B1
APPLICATION NO. : 10/452190
DATED : November 20, 2007
INVENTOR(S) : Thakor et al.

It is certified that error appears in the above-identified patent and that said Letters Patent is hereby corrected as shown below:

Column 1, lines 9-11, please delete "The invention was made under contracts with an agency of the U.S. Government under NIH#NS24282 and NIH#HL70129." and insert in its place --This invention was made with government support under Grant Nos. NS024282 and HL070129 awarded by NIH (National Institutes of Health). The government has certain rights in the invention.--

Signed and Sealed this
Twelfth Day of July, 2011

David J. Kappos
*Director of the United States Patent and Trademark Office*